(12) United States Patent
Lipsey et al.

(10) Patent No.: US 11,464,654 B2
(45) Date of Patent: Oct. 11, 2022

(54) MODULAR AND LIGHTWEIGHT MYOELECTRIC PROSTHESIS COMPONENTS AND RELATED METHODS

(71) Applicant: REHABILITATION INSTITUTE OF CHICAGO, Chicago, IL (US)

(72) Inventors: James Lipsey, Oak Park, IL (US); Jon Sensinger, Fredericton (CA)

(73) Assignee: REHABILITATION INSTITUTE OF CHICAGO, Chicago, IL (US)

( * ) Notice: Subject to any disclaimer, the term of this patent is extended or adjusted under 35 U.S.C. 154(b) by 193 days.

(21) Appl. No.: 16/448,756

(22) Filed: Jun. 21, 2019

(65) Prior Publication Data

US 2019/0380846 A1 Dec. 19, 2019

Related U.S. Application Data

(60) Continuation of application No. 15/806,209, filed on Nov. 7, 2017, now Pat. No. 10,369,016, which is a
(Continued)

(51) Int. Cl.
*A61F 2/58* (2006.01)
*A61F 2/72* (2006.01)
(Continued)

(52) U.S. Cl.
CPC .............. *A61F 2/582* (2013.01); *A61F 2/54* (2013.01); *A61F 2/58* (2013.01); *A61F 2/583* (2013.01);
(Continued)

(58) Field of Classification Search
CPC .............. A61F 2/582; A61F 2/54; A61F 2/58
See application file for complete search history.

(56) References Cited

U.S. PATENT DOCUMENTS 760,102 A 5/1904 Carnes
1,507,682 A 9/1924 Pecorella et al.
(Continued)

FOREIGN PATENT DOCUMENTS

CN 1803413 7/2006
CN 106994694 8/2017
(Continued)

OTHER PUBLICATIONS

Touch Bionics PowerPoint Presentation in 3 pages, believed to be shown at ISPO Conference in Leipzig, Germany, May 2016.
(Continued)

*Primary Examiner* — Bruce E Snow
(74) *Attorney, Agent, or Firm* — Knobbe, Martens, Olson & Bear, LLP

(57) ABSTRACT

Prosthetic devices and, more particularly, modular myoelectric prosthesis components and related methods, are described. In one embodiment, a hand for a prosthetic limb may comprise a rotor-motor; a transmission, comprising a differential roller screw; a linkage coupled to the transmission; and at least one finger coupled to the linkage. In one embodiment, a component part of a wrist of a prosthetic limb may comprise an exterior-rotor motor, a planetary gear transmission, a clutch, and a cycloid transmission. In one embodiment, an elbow for a prosthetic limb may comprise an exterior-rotor motor, and a transmission comprising a planetary gear transmission, a non-backdrivable clutch, and a screw.

16 Claims, 14 Drawing Sheets

Related U.S. Application Data division of application No. 14/614,231, filed on Feb. 4, 2015, now Pat. No. 9,839,534.

(60) Provisional application No. 61/935,836, filed on Feb. 4, 2014.

(51) Int. Cl.

| | | |
|---|---|---|
| *H02K 7/116* | (2006.01) | |
| *H02K 7/14* | (2006.01) | |
| *A61F 2/54* | (2006.01) | |
| *F16D 15/00* | (2006.01) | |
| *F16H 37/04* | (2006.01) | |
| *A61F 2/68* | (2006.01) | |
| *B25J 15/00* | (2006.01) | |
| *B25J 17/02* | (2006.01) | |
| *B25J 15/08* | (2006.01) | |
| *A61F 2/70* | (2006.01) | |
| *A61F 2/50* | (2006.01) | |
| *F16H 25/22* | (2006.01) | |
| *F16H 35/00* | (2006.01) | |

(52) U.S. Cl.
CPC .............. *A61F 2/585* (2013.01); *A61F 2/586* (2013.01); *A61F 2/72* (2013.01); *F16D 15/00* (2013.01); *F16H 37/041* (2013.01); *H02K 7/116* (2013.01); *H02K 7/14* (2013.01); *A61F 2002/5043* (2013.01); *A61F 2002/5072* (2013.01); *A61F 2002/543* (2013.01); *A61F 2002/587* (2013.01); *A61F 2002/6836* (2013.01); *A61F 2002/6845* (2013.01); *A61F 2002/6872* (2013.01); *A61F 2002/701* (2013.01); *A61F 2002/704* (2013.01); *A61F 2310/00047* (2013.01); *B25J 15/0009* (2013.01); *B25J 15/086* (2013.01); *B25J 17/0258* (2013.01); *F16H 25/2252* (2013.01); *F16H 2035/005* (2013.01)

(56) References Cited

U.S. PATENT DOCUMENTS

| | | |
|---|---|---|
| 1,507,683 A | 9/1924 | Pecorella et al. |
| 2,445,711 A | 7/1948 | Fitch |
| 2,477,463 A | 7/1949 | Otterman |
| 2,482,555 A | 9/1949 | Otterman |
| 2,508,156 A | 5/1950 | Gillman |
| 2,516,791 A | 7/1950 | Metis et al. |
| 2,586,293 A | 2/1952 | Birkigt |
| 2,592,842 A | 4/1952 | Alderson |
| 2,669,727 A | 2/1954 | Opuszenski |
| 2,983,162 A | 5/1961 | Musser |
| 3,406,584 A | 10/1968 | Roantree |
| 3,509,583 A | 5/1970 | Fraioli |
| 3,582,857 A | 6/1971 | Kishel |
| 3,641,832 A | 2/1972 | Shigeta et al. |
| 3,683,423 A | 8/1972 | Crapanzano |
| 3,751,995 A | 8/1973 | Carlson |
| 3,837,010 A | 9/1974 | Prout |
| 3,866,246 A | 2/1975 | Seamone et al. |
| 3,883,900 A | 5/1975 | Jerard et al. |
| 3,922,930 A | 12/1975 | Fletcher et al. |
| 4,030,141 A | 6/1977 | Graupe |
| 4,044,274 A | 8/1977 | Ohm |
| 4,114,464 A | 9/1978 | Schubert et al. |
| 4,197,592 A | 4/1980 | Klein |
| 4,398,110 A | 8/1983 | Flinchbaugh et al. |
| 4,558,704 A | 12/1985 | Petrofsky |
| 4,577,127 A | 3/1986 | Ferree et al. |
| 4,623,354 A | 11/1986 | Childress et al. |
| 4,678,952 A | 7/1987 | Peterson et al. |
| 4,808,187 A | 2/1989 | Patterson et al. |
| 4,813,303 A | 3/1989 | Beezer et al. |
| 4,822,238 A | 4/1989 | Kwech |
| 4,955,918 A | 9/1990 | Lee |
| 4,960,425 A | 10/1990 | Yan et al. |
| 4,990,162 A | 2/1991 | LeBlanc et al. |
| 5,020,162 A | 6/1991 | Kersten et al. |
| 5,062,673 A | 11/1991 | Mimura |
| 5,088,125 A | 2/1992 | Ansell et al. |
| 5,133,775 A | 7/1992 | Chen |
| 5,246,463 A | 9/1993 | Giampapa |
| 5,252,102 A | 10/1993 | Singer et al. |
| 5,387,245 A | 2/1995 | Fay et al. |
| 5,413,611 A | 5/1995 | Haslam, II et al. |
| 5,498,472 A | 3/1996 | Gold |
| 5,501,498 A | 3/1996 | Ulrich |
| 5,581,166 A | 12/1996 | Eismann et al. |
| 5,605,071 A | 2/1997 | Buchanan, Jr. |
| 5,650,704 A * | 7/1997 | Pratt ..................... B25J 9/10 |
| | | 318/560 |
| 5,785,960 A | 7/1998 | Rigg et al. |
| 5,851,194 A | 12/1998 | Fratrick |
| 5,852,675 A | 12/1998 | Matsuo et al. |
| 5,888,213 A | 3/1999 | Sears et al. |
| 5,888,246 A | 3/1999 | Gow |
| 6,111,973 A | 8/2000 | Holt et al. |
| 6,175,962 B1 | 1/2001 | Michelson |
| 6,223,615 B1 | 5/2001 | Huck |
| 6,244,873 B1 | 6/2001 | Hill et al. |
| 6,344,062 B1 | 2/2002 | Abboud et al. |
| 6,358,285 B1 | 3/2002 | Chen |
| 6,361,570 B1 | 3/2002 | Gow |
| 6,416,555 B1 | 7/2002 | Dillenburg et al. |
| 6,423,099 B1 | 7/2002 | Iversen et al. |
| 6,424,886 B1 | 7/2002 | Iversen et al. |
| 6,485,523 B2 | 11/2002 | Pierce et al. |
| 6,517,132 B2 | 2/2003 | Matsuda et al. |
| 6,582,473 B2 | 6/2003 | Pierce et al. |
| 6,591,707 B2 | 7/2003 | Torii et al. |
| 6,660,043 B2 | 12/2003 | Kajitani et al. |
| 6,786,112 B2 | 9/2004 | Ruttor |
| 6,846,331 B2 | 1/2005 | Senoir |
| 6,860,169 B2 | 3/2005 | Shinozaki |
| 6,921,419 B2 | 7/2005 | Weir et al. |
| 7,041,141 B2 | 5/2006 | Iversen et al. |
| 7,048,768 B1 | 5/2006 | Rouse et al. |
| 7,144,430 B2 | 12/2006 | Archer et al. |
| 7,243,569 B2 | 7/2007 | Takahashi et al. |
| 7,316,304 B2 | 1/2008 | Heravi et al. |
| 7,316,795 B1 | 1/2008 | Knauss |
| 7,370,896 B2 | 5/2008 | Anderson et al. |
| 7,438,726 B2 | 10/2008 | Erb |
| 7,640,680 B1 | 1/2010 | Castro |
| 7,655,051 B2 | 2/2010 | Stark |
| 7,823,475 B2 | 11/2010 | Hirabayashi et al. |
| 7,867,287 B2 | 1/2011 | Puchhammer |
| 7,914,587 B2 | 3/2011 | Archer et al. |
| 7,918,898 B2 | 4/2011 | Andrysek |
| 7,922,773 B1 | 4/2011 | Kuiken |
| 8,016,893 B2 | 9/2011 | Weinberg et al. |
| 8,021,435 B2 | 9/2011 | Bravo Castillo |
| 8,052,185 B2 | 11/2011 | Madhani |
| 8,058,823 B2 | 11/2011 | Horst et al. |
| 8,100,986 B2 | 1/2012 | Puchhammer et al. |
| 8,195,334 B2 | 6/2012 | Fukushima et al. |
| 8,197,554 B2 | 6/2012 | Whiteley et al. |
| 8,246,559 B2 | 8/2012 | Hoffman et al. |
| 8,257,446 B2 | 9/2012 | Puchhammer |
| 8,337,568 B2 | 12/2012 | Macduff |
| 8,414,658 B2 | 4/2013 | Johnson et al. |
| 8,449,624 B2 | 5/2013 | Evans et al. |
| 8,491,666 B2 | 7/2013 | Schulz |
| 8,579,991 B2 | 11/2013 | Puchhammer |
| 8,593,255 B2 | 11/2013 | Pang et al. |
| 8,597,212 B2 | 12/2013 | Kawakami et al. |
| 8,597,370 B2 | 12/2013 | Wisse et al. |
| 8,622,452 B2 | 1/2014 | Yamaguchi et al. |
| 8,657,887 B2 | 2/2014 | Gill |
| 8,662,552 B2 | 3/2014 | Torres-Jara |
| 8,663,339 B2 | 3/2014 | Inschlag et al. |

(56) References Cited

U.S. PATENT DOCUMENTS

| | | |
|---|---|---|
| 8,690,963 B2 | 4/2014 | Puchhammer |
| 8,696,763 B2 | 4/2014 | Gill |
| 8,739,315 B2 | 6/2014 | Baacke |
| 8,747,486 B2 | 6/2014 | Kawasaki et al. |
| 8,795,387 B1 | 8/2014 | Razink |
| 8,803,844 B1 | 8/2014 | Green et al. |
| 8,808,397 B2 | 8/2014 | Gow |
| 8,821,587 B2 | 9/2014 | Lanier et al. |
| 8,828,096 B2 | 9/2014 | Gill |
| 8,840,681 B2 | 9/2014 | Martin et al. |
| 8,900,327 B2 | 12/2014 | Bertels et al. |
| 8,915,969 B2 | 12/2014 | Boender |
| 8,920,519 B2 | 12/2014 | Johannes et al. |
| 8,951,303 B2 | 2/2015 | Dehoff et al. |
| 8,979,943 B2 | 3/2015 | Evans et al. |
| 8,984,736 B2 | 3/2015 | Radocy |
| 8,986,395 B2 | 3/2015 | McLeary |
| 8,995,760 B2 | 3/2015 | Gill |
| 9,028,560 B2 | 5/2015 | Farquharson et al. |
| 9,034,047 B2 | 5/2015 | Radocy |
| 9,072,614 B2 | 7/2015 | Starkey et al. |
| 9,084,690 B2 | 7/2015 | Pedersen et al. |
| 9,101,499 B2 | 8/2015 | Haggas |
| 9,114,028 B2 | 8/2015 | Langenfeld et al. |
| 9,114,030 B2 | 8/2015 | van der Merwe et al. |
| 9,121,699 B2 | 9/2015 | van der Merwe et al. |
| 9,265,625 B2 | 2/2016 | Goldfarb et al. |
| 9,278,012 B2 | 3/2016 | Gill |
| 9,320,621 B2 | 4/2016 | Iversen et al. |
| 9,333,096 B2 | 5/2016 | Perez de Alderete et al. |
| 9,381,099 B2 | 7/2016 | Perry et al. |
| 9,387,095 B2 | 7/2016 | McLeary et al. |
| 9,393,131 B2 | 7/2016 | Evans et al. |
| 9,402,749 B2 | 8/2016 | Gill et al. |
| 9,435,400 B2 | 9/2016 | Cheung et al. |
| 9,463,100 B2 | 10/2016 | Gill |
| 9,474,631 B2 | 10/2016 | Veatch |
| 9,486,925 B1 | 11/2016 | Stroop |
| 9,510,958 B2 | 12/2016 | Mori |
| 9,572,688 B2 | 2/2017 | Puchhammer |
| 9,579,218 B2 | 2/2017 | Lipsey et al. |
| 9,579,219 B2 | 2/2017 | Amend, Jr. et al. |
| 9,585,771 B2 | 3/2017 | Baba et al. |
| 9,687,362 B2 | 6/2017 | Mosadegh et al. |
| 9,707,103 B2 | 7/2017 | Thompson, Jr. et al. |
| 9,720,515 B2 | 8/2017 | Wagner et al. |
| 9,730,813 B2 | 8/2017 | Evans et al. |
| 9,737,418 B2 | 8/2017 | Veatch |
| 9,814,604 B2 | 11/2017 | Jury |
| 9,826,933 B2 | 11/2017 | van der Merwe et al. |
| 9,839,534 B2 | 12/2017 | Lipsey et al. |
| 9,861,499 B2 | 1/2018 | Sensinger |
| 9,861,500 B2 | 1/2018 | Puchhammer |
| 9,901,465 B2 | 2/2018 | Lanier, Jr. et al. |
| 9,931,229 B2 | 4/2018 | Veatch |
| 9,999,522 B2 | 6/2018 | Gill |
| 10,004,611 B2 | 6/2018 | Iversen et al. |
| 10,004,612 B2 | 6/2018 | Iversen et al. |
| 10,022,248 B2 | 7/2018 | Thompson, Jr. et al. |
| 10,034,780 B2 | 7/2018 | Lipsey et al. |
| 10,092,423 B2 | 10/2018 | Goldfarb et al. |
| 10,265,197 B2 | 4/2019 | Gill et al. |
| 10,318,863 B2 | 8/2019 | Lock et al. |
| 10,369,016 B2 | 8/2019 | Lipsey et al. |
| 10,369,024 B2 | 8/2019 | Gill |
| 10,398,576 B2 | 9/2019 | Gill et al. |
| 10,449,063 B2 | 10/2019 | Gill |
| 10,610,385 B2 | 4/2020 | Meijer et al. |
| 2001/0023058 A1 | 9/2001 | Jung et al. |
| 2002/0016631 A1 | 2/2002 | Marchitto et al. |
| 2002/0135241 A1 | 9/2002 | Kobayashi et al. |
| 2003/0036805 A1 | 2/2003 | Senior |
| 2004/0002672 A1 | 1/2004 | Carlson |
| 2004/0054423 A1 | 3/2004 | Martin |
| 2004/0078299 A1 | 4/2004 | Down-Logan et al. |
| 2004/0181289 A1 | 9/2004 | Bedard et al. |
| 2004/0182125 A1 | 9/2004 | McLean |
| 2005/0021154 A1 | 1/2005 | Brimalm |
| 2005/0021155 A1 | 1/2005 | Brimalm |
| 2005/0093997 A1 | 5/2005 | Dalton et al. |
| 2005/0101693 A1 | 5/2005 | Arbogast et al. |
| 2005/0102037 A1 | 5/2005 | Matsuda |
| 2005/0192677 A1 | 9/2005 | Ragnarsdottir et al. |
| 2006/0029909 A1 | 2/2006 | Kaczkowski |
| 2006/0054782 A1 | 3/2006 | Olsen et al. |
| 2006/0158146 A1 | 7/2006 | Tadano |
| 2006/0167564 A1 | 7/2006 | Flaherty et al. |
| 2006/0212129 A1 | 9/2006 | Lake et al. |
| 2006/0229755 A1 | 10/2006 | Kuiken et al. |
| 2006/0251408 A1 | 11/2006 | Konno et al. |
| 2007/0032884 A1 | 2/2007 | Veatch |
| 2007/0058860 A1 | 3/2007 | Harville et al. |
| 2007/0061111 A1 | 3/2007 | Jung et al. |
| 2007/0071314 A1 | 3/2007 | Bhatti et al. |
| 2007/0102228 A1 | 5/2007 | Shiina et al. |
| 2007/0137351 A1 | 6/2007 | Schwendemann |
| 2007/0230832 A1 | 10/2007 | Usui et al. |
| 2007/0260328 A1 | 11/2007 | Bertels et al. |
| 2007/0276303 A1 | 11/2007 | Jenner, Jr. |
| 2008/0058668 A1 | 3/2008 | Seyed Momen et al. |
| 2008/0097269 A1 | 4/2008 | Weinberg et al. |
| 2008/0146981 A1 | 6/2008 | Greenwald et al. |
| 2008/0215162 A1 | 9/2008 | Farnsworth et al. |
| 2008/0260218 A1 | 10/2008 | Smith et al. |
| 2008/0262634 A1 | 10/2008 | Puchhammer |
| 2009/0213379 A1 | 8/2009 | Carroll et al. |
| 2010/0016990 A1 | 1/2010 | Kurtz |
| 2010/0116078 A1 | 5/2010 | Kim |
| 2010/0262260 A1* | 10/2010 | Bedard ............... A61F 2/64 623/33 |
| 2010/0274365 A1 | 10/2010 | Evans et al. |
| 2011/0048098 A1 | 3/2011 | Rollins et al. |
| 2011/0203027 A1 | 8/2011 | Flather et al. |
| 2011/0237381 A1 | 9/2011 | Puchhammer |
| 2011/0257765 A1 | 10/2011 | Evans et al. |
| 2011/0264238 A1 | 10/2011 | van der Merwe et al. |
| 2011/0265597 A1 | 11/2011 | Long |
| 2011/0278061 A1 | 11/2011 | Farnan |
| 2012/0004884 A1 | 1/2012 | Flllol et al. |
| 2012/0014571 A1 | 1/2012 | Wong et al. |
| 2012/0061155 A1 | 3/2012 | Berger et al. |
| 2012/0099788 A1 | 4/2012 | Bhatti et al. |
| 2012/0109337 A1 | 5/2012 | Schulz |
| 2012/0123558 A1 | 5/2012 | Gill |
| 2012/0204665 A1 | 8/2012 | Baudasse |
| 2012/0280812 A1 | 11/2012 | Sheikman et al. |
| 2012/0286629 A1 | 11/2012 | Johnson et al. |
| 2012/0303136 A1 | 11/2012 | Macduff |
| 2012/0330439 A1 | 12/2012 | Goldfarb et al. |
| 2013/0041476 A1 | 2/2013 | Schulz |
| 2013/0053984 A1 | 2/2013 | Hunter et al. |
| 2013/0076699 A1 | 3/2013 | Spencer |
| 2013/0144197 A1 | 6/2013 | Ingimundarson et al. |
| 2013/0175816 A1 | 7/2013 | Kawasaki et al. |
| 2013/0253705 A1 | 9/2013 | Goldfarb et al. |
| 2013/0268090 A1 | 10/2013 | Goldfarb et al. |
| 2013/0268094 A1 | 10/2013 | Van Wiemeersch |
| 2013/0310949 A1 | 11/2013 | Goldfarb et al. |
| 2014/0236314 A1 | 8/2014 | Van Wiemeersch |
| 2014/0251056 A1 | 9/2014 | Preuss |
| 2014/0324189 A1 | 10/2014 | Gill et al. |
| 2014/0371871 A1 | 12/2014 | Farina et al. |
| 2015/0112448 A1 | 4/2015 | Scott et al. |
| 2015/0142082 A1 | 5/2015 | Simon et al. |
| 2015/0183069 A1 | 7/2015 | Lee |
| 2015/0216681 A1 | 8/2015 | Lipsey et al. |
| 2015/0230941 A1 | 8/2015 | Jury |
| 2015/0351935 A1 | 12/2015 | Donati et al. |
| 2015/0360369 A1 | 12/2015 | Ishikawa et al. |
| 2015/0366678 A1 | 12/2015 | Edwards et al. |
| 2015/0374515 A1 | 12/2015 | Meijer et al. |
| 2016/0166409 A1 | 6/2016 | Goldfarb et al. |
| 2016/0250044 A1 | 9/2016 | Iversen et al. |
| 2016/0287422 A1 | 10/2016 | Kelly et al. |

(56) References Cited

U.S. PATENT DOCUMENTS

| | | |
|---|---|---|
| 2016/0374833 A1 | 12/2016 | Dechev et al. |
| 2017/0007424 A1 | 1/2017 | Gill |
| 2017/0049583 A1 | 2/2017 | Belter et al. |
| 2017/0049586 A1 | 2/2017 | Gill et al. |
| 2017/0209288 A1 | 7/2017 | Veatch |
| 2017/0266020 A1 | 9/2017 | Glasgow |
| 2017/0281368 A1 | 10/2017 | Gill |
| 2018/0036145 A1 | 2/2018 | Jury et al. |
| 2018/0064563 A1 | 3/2018 | Gill |
| 2018/0098862 A1 | 4/2018 | Kuiken et al. |
| 2018/0133028 A1 | 5/2018 | Poirters |
| 2018/0140442 A1 | 5/2018 | Thomas |
| 2018/0168477 A1 | 6/2018 | Graimann et al. |
| 2018/0168830 A1 | 6/2018 | Evans et al. |
| 2018/0235782 A1 | 8/2018 | Choi et al. |
| 2018/0250146 A1 | 9/2018 | Glasgow |
| 2018/0289510 A1 | 10/2018 | Muller et al. |
| 2018/0296368 A1 | 10/2018 | Gill |
| 2018/0296369 A1 | 10/2018 | Smit et al. |
| 2018/0303633 A1 | 10/2018 | Yi |
| 2018/0311827 A1 | 11/2018 | Bicchi et al. |
| 2018/0325701 A1 | 11/2018 | Ortiz Catalan et al. |
| 2018/0338843 A1 | 11/2018 | Kalmar et al. |
| 2019/0091040 A1 | 3/2019 | Gill |
| 2019/0183661 A1 | 6/2019 | Gill |
| 2019/0209345 A1 | 7/2019 | LaChappelle |
| 2019/0216618 A1 | 7/2019 | Gill |
| 2019/0343660 A1 | 11/2019 | Gill |
| 2020/0054466 A1 | 2/2020 | Gill et al. |
| 2020/0197193 A1 | 6/2020 | Byrne et al. |

FOREIGN PATENT DOCUMENTS

| | | |
|---|---|---|
| DE | 309 367 | 11/1918 |
| DE | 24 34 834 | 2/1976 |
| DE | 198 54 762 | 6/2000 |
| DE | 101 05 814 | 9/2002 |
| DE | 203 15 575 | 1/2004 |
| DE | 698 16 848 | 4/2004 |
| DE | 10 2012 009 699 | 11/2013 |
| EP | 0 145 504 | 6/1985 |
| EP | 0 219 478 | 4/1987 |
| EP | 0 256 643 | 2/1988 |
| EP | 0 484 173 | 5/1992 |
| EP | 0 947 899 | 10/1999 |
| EP | 0 968 695 | 1/2000 |
| EP | 1 043 003 | 10/2000 |
| EP | 1 277 451 | 1/2003 |
| EP | 1 522 286 | 4/2005 |
| EP | 1 617 103 | 1/2006 |
| EP | 1 982 800 | 10/2008 |
| EP | 1 820 610 | 4/2009 |
| EP | 1 962 732 | 8/2009 |
| EP | 1 557 547 | 1/2011 |
| EP | 1 971 297 | 3/2012 |
| EP | 2 532 927 | 12/2012 |
| EP | 2 612 619 | 7/2013 |
| EP | 2 616 017 | 7/2013 |
| EP | 2 653 137 | 10/2013 |
| EP | 2 664 302 | 11/2013 |
| EP | 2 454 055 | 12/2013 |
| EP | 2 114 316 | 7/2014 |
| EP | 2 523 636 | 7/2015 |
| EP | 2 114 315 | 5/2016 |
| EP | 2 419 056 | 5/2016 |
| EP | 2 890 333 | 12/2016 |
| EP | 2 696 814 | 1/2017 |
| GB | 326 970 | 3/1930 |
| GB | 607 001 | 2/1947 |
| GB | 1 386 942 | 3/1975 |
| GB | 1 510 298 | 5/1978 |
| GB | 1 585 256 | 2/1981 |
| GB | 2 067 074 | 7/1981 |
| GB | 2 146 406 | 4/1985 |
| GB | 2 357 725 A | 7/2001 |
| GB | 2 444 679 | 6/2008 |
| JP | 53-011456 | 2/1978 |
| JP | 53-094693 | 8/1978 |
| JP | 07-174631 | 7/1995 |
| JP | 2001-082913 | 3/2001 |
| JP | 2001-299448 | 10/2001 |
| JP | 2002-131135 | 5/2002 |
| JP | 2002-310242 | 10/2002 |
| JP | 2003-134526 | 5/2003 |
| JP | 2004-073802 | 3/2004 |
| JP | 2004-224280 | 8/2004 |
| JP | 2018-167375 | 11/2018 |
| WO | WO 95/024875 | 9/1995 |
| WO | WO 96/023643 | 8/1996 |
| WO | WO 99/021517 | 5/1999 |
| WO | WO 00/025840 | 5/2000 |
| WO | WO 00/069375 | 11/2000 |
| WO | WO 01/004838 | 1/2001 |
| WO | WO 02/049534 | 6/2002 |
| WO | WO 03/017877 | 3/2003 |
| WO | WO 03/017878 | 3/2003 |
| WO | WO 03/017880 | 3/2003 |
| WO | WO 2006/058190 | 6/2006 |
| WO | WO 2006/069264 | 6/2006 |
| WO | WO 2006/078432 | 7/2006 |
| WO | WO 2006/086504 | 8/2006 |
| WO | WO 2006/092604 | 9/2006 |
| WO | WO 2006/110790 | 10/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |
| WO | WO 2007/127973 | 11/2007 |
| WO | WO 2008/044052 | 4/2008 |
| WO | WO 2008/044207 | 4/2008 |
| WO | WO 2008/092695 | 8/2008 |
| WO | WO 2008/098059 | 8/2008 |
| WO | WO 2008/098072 | 8/2008 |
| WO | WO 2009/011682 | 1/2009 |
| WO | WO 2010/018358 | 2/2010 |
| WO | WO 2010/051798 | 5/2010 |
| WO | WO 2010/149967 | 12/2010 |
| WO | WO 2011/001136 | 1/2011 |
| WO | WO 2011/022569 | 2/2011 |
| WO | WO 2011/036473 | 3/2011 |
| WO | WO 2011/036626 | 3/2011 |
| WO | WO 2011/088964 | 7/2011 |
| WO | WO 2011/107778 | 9/2011 |
| WO | WO 2011/143004 | 11/2011 |
| WO | WO 2014/027897 | 2/2014 |
| WO | WO 2015/120076 | 8/2015 |
| WO | WO 2015/120083 | 8/2015 |
| WO | WO 2016/051138 | 4/2016 |
| WO | WO 2017/061879 | 4/2017 |
| WO | WO 2017/199127 | 11/2017 |
| WO | WO 2018/006722 | 1/2018 |
| WO | WO 2018/054945 | 3/2018 |
| WO | WO 2018/121983 | 7/2018 |
| WO | WO 2018/158554 | 9/2018 |
| WO | WO 2018/178420 | 10/2018 |
| WO | WO 2018/180782 | 10/2018 |
| WO | WO 2018/187800 | 10/2018 |

OTHER PUBLICATIONS

Touch Bionics PowerPoint Slide in 1 page, believed to be presented at Advanced Arm Dynamics company Jan. 11, 2016.

Touch Bionics Screenshots of video in PowerPoint Presentation in 4 pages, believed to be shown at ISPO Conference in Leipzig, Germany, May 2016.

9 Worm Gear Pair, KHK Technical Information, Oct. 21, 2008, pp. 291-299.

Ama, Excerpts from American Medical Association, Guides to the Evaluation of Permanent Impairment (5th ed. 2000), pp. 432-453.

Bretthauer et al., "A New Adaptive Hand Prosthesis", Handchirurgie Mikrochirurgie Plastische Chirurgie, Feb. 2008, pp. 40-45.

(56) References Cited

OTHER PUBLICATIONS

Kargov et al., "Applications of a Fluidic Artificial Hand in the Field of Rehabilitation", Rehabilitation Robotics, Ch. 15, Aug. 2007, pp. 261-286.
Kawasaki et al., "Design and Control of Five-Fingered Haptic Interface Opposite to Human Hand", IEEE Transactions on Robotics, Oct. 2007, vol. 23, No. 5., pp. 909-918.
MEC '05: Integrating Prosthetics and Medicine, University of New Brunswick's MyoElectric Controls/Powered Prosthetics Symposium, Aug. 17-19, 2005, Fredericton NB Canada, pp. 260.
"Motor Technology—Girard Gearboxes Low Backlash Principle Explained", Motor Technology, https://www.motec.co.uk/tip-gearbox_principle.htm as printed May 23, 2012 in 3 pages.
Schulz et al., "Die Entwicklung Einer Multifunktionalen Kosmetischen Handprothese", Prothetik, Orthopädie-Technik Aug. 2006, pp. 627-632.
The Weir Thesis ("Weir Thesis") is entitled "An Externally-Powered, Myo-Electrically Controlled Synergetic Prosthetic Hand for the Partial-Hand Amputee", published Aug. 1989, pp. 365.
Albu-Schäffer et al., "Soft Robotics", IEEE Robotics & Automation Magazine, Sep. 2008, vol. 15, No. 3, pp. 20-30.
Antonio et al., "A Virtual Upper Limb Prosthesis as a Training System", 7th International Conference on Electrical Engineering, Computing Science and Automatic Control (CCE 2010) Tuxtla Gutiérrez, Chiapas, México. Sep. 8-10, 2010, pp. 210-215.
Bellman et al., "SPARKy 3: Design of an Active Robotic Ankle Prosthesis with Two Actuated Degrees of Freedom Using Regenerative Kinetics", in Proceedings of the 2nd Biennial IEEE/RAS-EMBS International Conference on Biomedical Robotics and Biomechatronics, Oct. 19-22, 2008, Scottsdale, AZ, pp. 511-516.
Belter et al., "Mechanical Design and Performance Specifications of Anthropomorphic Prosthetic Hands: A Review", JRRD, Jan. 2013, vol. 50, No. 5, pp. 599-618.
Biddiss et al., "Consumer Design Priorities for Upper Limb Prosthetics", Disability and Rehabilitation: Assistive Technology, Nov. 2007, vol. 2, No. 6, pp. 346-357.
Biddiss et al., "Upper Limb Prosthesis Use and Abandonment: A Survey of the Last 25 Years", Prosthetics and Orthotics International, Sep. 2007, vol. 31, No. 3, pp. 236-257.
Biddiss et al., "Upper-Limb Prosthetics: Critical Factors in Device Abandonment", American Journal of Physical Medicine & Rehabilitation, Dec. 2007, vol. 86, No. 12, pp. 977-987.
Chicoine et al., "Prosthesis-Guided Training of Pattern Recognition-Controlled Myoelectric Prosthesis", in Proceedings of the 34th Annual International Conference of the IEEE EMBS, San Diego, CA, Aug. 28-Sep. 1, 2012, pp. 1876-1879.
Childress et al., "Control of Limb Prostheses", American Academy of Orthopaedic Surgeons, Chapter 12, pp. 173-195, 2004.
Choi et al., "Design of High Power Permanent Magnet Motor with Segment Rectangular Copper Wire and Closed Slot Opening on Electric Vehicles", IEEE Transactions on Magnetics, Jun. 2010, vol. 46, No. 9, pp. 2070-2073.
Cipriani et al., "On the Shared Control of an EMG-Controlled Prosthetic Hand: Analysis of User-Prosthesis Interaction", IEEE Transactions on Robotics, Feb. 2008, vol. 24, No. 1, pp. 170-184.
Connolly, "Prosthetic Hands from Touch Bionics", Industrial Robot, Emerald Group Publishing Limited, 2008, vol. 35, No. 4, pp. 290-293.
Controzzi et al., "Miniaturized Non-Back-Drivable Mechanism for Robotic Applications", Mechanism and Machine Theory, Oct. 2010, vol. 45, No. 10, pp. 1395-1406.
Damian et al., "Artificial Tactile Sensing of Position and Slip Speed by Exploiting Geometrical Features", IEEE/ASME Transactions on Mechatronics, Feb. 2015, vol. 20, No. 1, pp. 263-274.
"DC Circuit Theory", https://www.electronics-tutorials.ws/dccircuits/dcp_1.html, Date verified by the Wayback Machine Apr. 23, 2013, pp. 16.
Dechev et al., "Multiple Finger, Passive Adaptive Grasp Prosthetic Hand", Mechanism and Machine Theory, Oct. 1, 2001, vol. 36, No. 10, pp. 1157-1173.

Dellorto, Danielle, "Bionic Hands Controlled by iPhone App", CNN, Apr. 12, 2013, pp. 4 http://www.cnn.com/2013/04/12/heaith/bionic-hands.
"DuPont Engineering Design—The Review of DuPont Engineering Polymers in Action", http://www.engpolymer.co.kr/x_data/magazine/engdesign07_2e.pdf, 2007, pp. 16.
Engeberg et al., "Adaptive Sliding Mode Control for Prosthetic Hands to Simultaneously Prevent Slip and Minimize Deformation of Grasped Objects," IEEE/ASME Transactions on Mechatronics, Feb. 2013, vol. 18, No. 1, pp. 376-385.
Fougner et al., "Control of Upper Limb Prostheses: Terminology and Proportional Myoelectric Control—A Review", IEEE Transactions on Neural Systems Rehabilitation Engineering, Sep. 2012, vol. 20, No. 5, pp. 663-677.
Fukuda et al., "Training of Grasping Motion Using a Virtual Prosthetic Control System", 2010 IEEE International Conference on Systems Man and Cybernetics (SMC), Oct. 10-13, 2010, pp. 1793-1798.
Gaine et al., "Upper Limb Traumatic Amputees. Review of Prosthetic Use", The Journal of Hand Surgery, Feb. 1997, vol. 22B, No. 1, pp. 73-76.
Grip Chips™, Datasheet, May 15, 2014, Issue 1, http://touchbionics.com/sites/default/files/files/Grip%20Chip%20datasheet%20May%202014.pdf, pp. 1.
Heckathorne, Craig W., "Components for Electric-Powered Systems", American Academy of Orthopaedic Surgeons, Chapter 11, pp. 145-171, 2004.
Hojjat et al., "A Comprehensive Study on Capabilities and Limitations of Roller-Screw with Emphasis on Slip Tendency", Mechanism and Machine Theory, 2009, vol. 44, No. 10, pp. 1887-1899.
Hsieh, Chiu-Fan., "Dynamics Analysis of Cycloidal Speed Reducers with Pinwheel and Nonpinwheel Designs", ASME Journal of Mechanical Design, Sep. 2014, vol. 136, No. 9, pp. 091008-1-091008-11.
International Search Report and Written Opinion in Application No. PCT/US2015/014497, dated Jul. 24, 2015.
International Search Report and Written Opinion in Application No. PCT/US2015/014505, dated Apr. 21, 2015.
Jebsen et al., "An Objective and Standardized Test of Hand Function", Archives of Physical Medicine and Rehabilitation, Jun. 1969, vol. 50, No. 6, pp. 311-319.
Johannes et al., "An Overview of the Developmental Process for the Modular Prosthetic Limb," John Hopkins APL Technical Digest, 2011, vol. 30, No. 3, pp. 207-216.
Kent et al., "Electromyogram Synergy Control of a Dexterous Artificial Hand to Unscrew and Screw Objects", Journal of Neuroengineering and Rehabilitation, 2014, vol. 11, No. 1, pp. 1-20.
Kermani et al., "Friction Identification and Compensation in Robotic Manipulators", IEEE Transactions on Instrumentation and Measurement, Dec. 2007, vol. 56, No. 6, pp. 2346-2353.
Kuiken et al., "Targeted Muscle Reinnervation for Real-Time Myoelectric Control of Multifunction Artificial Arms", JAMA, Feb. 11, 2009, vol. 301, No. 6, pp. 619-628.
Kyberd et al., "Two-Degree-of-Freedom Powered Prosthetic Wrist", Journal of Rehabilitation Research & Development, 2011, vol. 48, No. 6, pp. 609-617.
Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.
Light et al., "Establishing a Standardized Clinical Assessment Tool of Pathologic and Prosthetic Hand Function: Normative Data, Reliability, and Validity", Archives of Physical Medicine and Rehabilitation, Jun. 2002, vol. 83, pp. 776-783.
Mace et al., "Augmenting Neuroprosthetic Hand Control Through Evaluation of a Bioacoustic Interface", IEEE/RSJ International Conference on Intelligent Robots and Systems (IROS), Tokyo, Japan, Nov. 3-7, 2013, pp. 7.
Majd et al., "A Continuous Friction Model for Servo Systems with Stiction", in Proceedings of the IEEE Conference on Control Applications, 1995, pp. 296-301.

(56) References Cited

OTHER PUBLICATIONS

Martinez-Villalpando et al., "Agonist-Antagonist Active Knee Prosthesis: A Preliminary Study in Level-Ground Walking", Journal of Rehabilitation Research & Development, vol. 46, No. 3, 2009, pp. 361-374.

Maxon Precision Motors, Inc., "Maxon Flat Motor: EX 10 flat 10 mm, brushless, 0.25 Watt", Specification, May 2011, p. 181.

Maxon Precision Motors, Inc., "Maxon EC Motor: EC10 10 mm, brushless, 8 Watt", Specification, May 2011, p. 140.

Miller et al., "Summary and Recommendations of the Academy's State of the Science Conference on Upper Limb Prosthetic Outcome Measures", Journal of Prosthetics Orthotics, 2009, vol. 21, pp. 83-89.

Montagnani et al., "Is it Finger or Wrist Dexterity that is Missing in Current Hand Prostheses?", IEEE Transactions on Neural Systems and Rehabilitation Engineering, Jul. 2015, vol. 23, No. 4, pp. 600-609.

Morita et al., "Development of 4-D.O.F. Manipulator Using Mechanical Impedance Adjuster", Proceedings of the 1996 IEEE International Conference on Robotics and Automation, Minneapolis, MN, Apr. 1996, pp. 2902-2907.

Ninu et al., "Closed-Loop Control of Grasping with a Myoelectric Hand Prosthesis: Which are the Relevant Feedback Variable for Force Control?" IEEE Transactions on Neural Systems and Rehabilitation Engineering, Sep. 2014, vol. 22, No. 5, pp. 1041-1052.

Osborn et al., "Utilizing Tactile Feedback for Biomimetic Grasping Control in Upper Limb Prostheses". Department of Biomedical Engineering, Johns Hopkins University, Baltimore, USA, 2013, pp. 4.

Pedrocchi et al., "MUNDUS Project: Multimodal Neuroprosthesis for Daily Upper Limb Support", Journal of Neuroengineering and Rehabilitation, 2013, vol. 10, No. 66, pp. 20. http://www.ineuroengrehab.com/content/10/1/66.

Pinzur et al., "Functional Outcome Following Traumatic Upper Limb Amputation and Prosthetic Limb Fitting", J. Hand Surgery, Amer. vol., 1994. vol. 19, pp. 836-839.

Press Release, "Touch Bionics Introduce Digitally Controlled Supro Wrist", http://www.touchbionics.com/news-events/news/touch-bionics-introduce-digitally-controlled-supro-wrist, May 3, 2016 in 2 pages.

Raspopovic et al., "Restoring Natural Sensory Feedback in Real-Time Bidirectional Hand Prostheses", Science Translational Medicine, Feb. 5, 2014, vol. 6, No. 222, pp. 1-10.

Resnik et al., "The DEKA Arm: Its Features, Functionality, and Evolution During the Veterans Affairs Study to Optimize the DEKA Arm", Prosthetics and Orthotics International, 2014, vol. 38, No. 6, pp. 492-504.

Scheme et al., "Electromyogram Pattern Recognition for Control of Powered Upper-Limb Prostheses: State of the Art and Challenges for Clinical Use", Journal of Rehabilitation Research & Development (JRRD), 2011, vol. 48, No. 6, pp. 643-659.

Scheme et al., "Motion Normalized Proportional Control for Improved Pattern Recognition-Based Myoelectric Control", IEEE Transactions on Neural Systems and Rehabilitation Engineering, Jan. 2014, vol. 22, No. 1, pp. 149-157.

Sensinger et al., "Cycloid vs. Harmonic Drives for use in High Ratio, Single Stage Robotic Transmissions", 2012 IEEE Conference on Robotics and Automation (ICRA), Saint Paul, MN, USA, May 14-18, 2012, pp. 4130-4135.

Sensinger, "Efficiency of High-Sensitivity Gear Trains, such as Cycloid Drives", Journal of Mechanical Design, Jul. 2013, vol. 135, No. 7, pp. 071006-1-071006-9.

Sensinger et al., "Exterior vs. Interior Rotors in Robotic Brushless Motors", 2011 IEEE International Conference on Robotics and Automation (ICRA), Shanghai, China, May 9-13, 2011, pp. 2764-2770.

Sensinger, "Selecting Motors for Robots Using Biomimetic Trajectories: Optimum Benchmarks, Windings, and other Considerations," 2010 IEEE International Conference on Robotics and Automation (ICRA), Anchorage, AL, USA, May 3-8, 2010, pp. 4175-4181.

Sensinger, "Unified Approach to Cycloid Drive Profile, Stress, and Efficiency Optimization", Journal of Mechanical Design, Feb. 2010, vol. 132, pp. 024503-1-024503-5.

Sensinger et al., "User-Modulated Impedance Control of a Prosthetic Elbow in Unconstrained, Perturbed Motion", IEEE Transactions on Biomedical Engineering, Mar. 2008, vol. 55, No. 3, pp. 1043-1055.

Stix, Gary, "Phantom Touch: Imbuing a Prosthesis with Manual Dexterity", Scientific American, Oct. 1998, pp. 41 & 44.

"Supro Wrist", Touch Bionics, https://web.archive.org/web/20160928141440/http://www.touchbionics.com/products/supro-wrist as Archived Sep. 28, 2016 in 3 pages.

Sutton et al., "Towards a Universal Coupler Design for Modern Powered Prostheses", MEG 11 Raising the Standard, Proceedings of the 2011 MyoElectric Controls/Powered Prosthetics Symposium Frederiction, New Brunswick, Canada, Aug. 14-19, 2011, pp. 5.

Tan et al., "A Neural Interface Provides Long-Term Stable Natural Touch Perception", Science Translational Medicine, Oct. 8, 2014, vol. 6, No. 257, pp. 1-11.

Tang, "General Concepts of Wrist Biomechanics and a View from Other Species", The Journal of Hand Surgery, European Volume, Aug. 2008, vol. 33, No. 4, pp. 519-525.

Toledo et al., "A Comparison of Direct and Pattern Recognition Control for a Two Degree-of-Freedom Above Elbow Virtual Prosthesis", in Proceedings 34th Annual International Conference of the IEEE EMBS, 2012, pp. 4332-4335.

"Touch Bionics Grip Chips Let Hand Prostheses Think for Themselves", May 15, 2014, www.medgadget.com/2014/05/touch-bionics-grip-chips-let-hand-prostheses-think-for-themselves.html, pp. 2.

Trachtenberg et al., "Radio Frequency Identification, An Innovative Solution to Guide Dexterous Prosthetic Hands", 33rd Annual International Conference of the IEEE EMBS, Boston, MA, Aug. 30-Sep. 3, 2011, pp. 4.

Vilarino, Martin, "A Novel Wireless Controller for Switching among Modes for an Upper-Limb Prosthesis", The Academy Today, Jan. 2014, vol. 10, No. 1, pp. A-12 to A-15.

Weir et al., "Design of Artificial Arms and Hands for Prosthetic Applications", Biomedical Engineering and Design Handbook, 2009, vol. 2, pp. 537-598.

Wettels et al., "Grip Control Using Biomimetic Tactile Sensing Systems", IEEE/ASME Transactions on Mechatronics, Dec. 2009, vol. 14, No. 6, pp. 718-723.

Whiteside et al., "Practice Analysis Task Force: Practice Analysis of the Disciplines of Orthotics and Prosthetics", American Board for Certification in Orthotics and Prosthetics, Inc., 2000, pp. 1-51.

Wilson et al., "A Bus-Based Smart Myoelectric Electrode/Amplifier-System Requirements", IEEE Transactions on Instrumentation and Measurement, Oct. 2011, vol. 60, No. 10, pp. 3290-3299.

Zampagni et al., "A Protocol for Clinical Evaluation of the Carrying Angle of the Elbow by Anatomic Landmarks", Journal of Shoulder and Elbow Surgery, 2008, vol. 17, No. 1, pp. 106-112.

\* cited by examiner

MODULAR AND LIGHTWEIGHT MYOELECTRIC PROSTHESIS COMPONENTS AND RELATED METHODS

CROSS-REFERENCE TO RELATED APPLICATIONS

The present application is a continuation of U.S. patent application Ser. No. 15/806,209, filed on Nov. 7, 2017, now U.S. Pat. No. 10,369,016, which is a divisional of U.S. patent application Ser. No. 14/614,231, filed on Feb. 4, 2015, now U.S. Pat. No. 9,839,534, which claims priority to U.S. Provisional Patent Application No. 61/935,836, filed on Feb. 4, 2014, each of which is incorporated herein by reference in its entirety.

STATEMENT REGARDING FEDERALLY SPONSORED RESEARCH OR DEVELOPMENT

This invention was made with government support under W81XWH-11-1-0720 and W81XWH-10-2-0033 awarded by the United States Army. The government has certain rights in the invention.

TECHNICAL FIELD

The present disclosure is generally directed to prosthetic devices and, more particularly, to modular myoelectric prosthesis components and related methods.

BACKGROUND

Amputation of the arm causes significant disability, which is most effectively treated by replacement of the missing limb with a prosthetic device. Body-powered prostheses use a Bowden cable that couples motion of an intact joint to movement of the terminal device. Myoelectric prostheses control motorized joints via commands sent through the patients' residual muscles and sensed by surface electrodes embedded in the prosthetic socket.

Advances in embedded controllers, battery density, and motor design have increased the number of myoelectric prosthesis users. However, existing myoelectric prostheses are heavy, and wearing them constantly does not appeal to many amputees. Additionally, such prostheses are often too large for many amputees, such as children and many women. Several multi-function arms have recently come on the market, including Otto Bock's Michelangelo Hand, the Touch Bionics Hand, the BeBionics Hand, and the Vincent Hand. These devices are typically designed for a 50th percentile male (22.2 cm/8.75" hand circumference). Other hands are being developed in research, but use components that limit the strength, weight, and small volumes the limbs can achieve.

SUMMARY

In one embodiment, a hand for a prosthetic limb may comprise a rotor-motor, a transmission, comprising a differential roller screw; a linkage coupled to the transmission; at least one finger coupled to the linkage; wherein the rotor-motor is configured to actuate the transmission, the transmission is configured to actuate the linkage, and the linkage is configured to flex or extend the at least one finger. At least one finger of the hand may comprise an index finger and middle finger. The index finger and the middle finger may be fused. At least one finger may comprise an independently hinged finger, such as a ring finger or a pinky finger. The hand may comprise a side bar coupled to the transmission for transmitting motion to at least one of the independently hinged fingers. The linkage of the hand may generate an anatomically natural motion. The hand may further comprise a controller for the control of the hand. The hand may comprise an exoskeleton, which may be made from aluminium. A portion of the exoskeleton may be attachable to a wrist flexor. The rotor-motor of the hand may be a brushless interior rotor motor. The transmission of the hand may further comprise a gear set comprising at least one gear, the gear set positioned between the rotor-motor and the differential roller screw, the gear set adapted to translate rotational motion from the rotor-motor into linear motion of the differential roller screw. The transmission may further comprise a non-backdrivable clutch. The clutch may comprise a cam comprising an annulus, an input side that is adapted to receive an input force, and an output side that is adapted to provide an output force; a pin and a roller, each located adjacent to the input side of the cam; wherein the cam is adapted so that movement of the cam in response to the input force causes the pin to push the roller out of contact with the annulus, when a force is applied to the input side of the cam, the pin pushes the roller out of contact with the annulus to allow for movement of the cam. The transmission may further comprise a gear set comprising at least one gear, the gear set positioned between the rotor-motor and the differential roller screw, the gear set adapted to translate rotational motion from the rotor-motor into linear motion of the differential roller screw. The hand may further comprising a casing for housing the differential roller screw. The cam may be positioned at the base of the hand, the casing may have a proximal end that is adjacent to the cam, and the casing may be positioned in the interior of the hand. The clutch may further comprise a mechanical fuse. The linkage of the hand may be coupled to the transmission via a pivot. The hand may further comprise a thumb comprising exactly one motor and a gear set comprising at least one gear, wherein the motor actuates only the thumb. The hand may be adapted to be positioned in more than one, or in all, of the following positions: relaxed, palm-flat, chuck grip, and cylindrical grip.

In one embodiment, a wrist for a prosthetic limb may comprise a wrist rotator comprising a first exterior-rotor motor, a first planetary gear transmission, a first clutch and a first cycloid transmission, in a transmission arrangement such that actuation of the first exterior-rotor motor causes movement through the first planetary gear transmission, first clutch, and first cycloid transmission to cause rotation of the wrist; and a wrist flexor comprising a second exterior-rotor motor, a second planetary gear transmission, a second clutch and a second cycloid transmission, in a transmission arrangement such that actuation of the second exterior-rotor motor causes movement through the second planetary gear transmission second first clutch, and second cycloid transmission to cause flexion of the wrist. The first clutch may comprise a non-backdrivable mechanism for preventing output motion of the first clutch to be transmitted to the first cycloid transmission. The second clutch may comprise a non-backdrivable mechanism for preventing output motion of the first clutch to be transmitted to the first cycloid transmission. At least one of the first planetary gear transmission and the second planetary gear transmission may be a single-stage planetary gear transmission. The torque ratio of the first planetary gear transmission may be about 3.71:1 and the torque ratio of the first cycloid transmission may be about 16:1. The wrist may comprise an interface on the wrist rotator for transmitting signals across an access of rotation of the wrist rotator. The interface may comprise an interface for power signals and an interface for ground signals. The interface may further comprise an interface for at least two communication signals. The wrist may comprise a mechanical stop to limit motion of the wrist flexor. The wrist rotator and the wrist flexor may be connected by a coupler that allows for the transmission of power from the wrist rotator to the wrist flexor. The wrist flexor may be set on a rotation axis skewed by between about 10 to 30 degrees to provide radial/ulnar deviation. The non-backdrivable mechanism may comprise a plurality of rollers and a plurality of springs.

In one embodiment, a component part of a wrist of a prosthetic limb may comprise an exterior-rotor motor, a planetary gear transmission, a clutch, and a cycloid transmission. The exterior-rotor motor, a planetary gear transmission, a clutch, and a cycloid transmission may be in a transmission arrangement such that actuation of the exterior-rotor motor causes movement through the planetary gear transmission, clutch, and cycloid transmission to cause movement of the wrist. The clutch may comprise a non-backdrivable mechanism for preventing output motion of the clutch to be transmitted to the cycloid transmission. The planetary gear transmission may be a single-stage planetary gear transmission. The movement of the wrist may be a rotational movement. The torque ratio of the planetary gear transmission may be about 3.71:1 and the torque ratio of the cycloid transmission may be about 16:1. The movement of the wrist may be a flexion movement. The wrist component may be set on a rotation axis skewed by between about 10 to 30 degrees to provide radial/ulnar deviation.

In one embodiment, an elbow for a prosthetic limb may comprise an exterior-rotor motor, and a transmission comprising a planetary gear transmission, a non-backdrivable clutch, and a screw. The screw may be adapted to receive a rotational force in a first direction from the clutch, and in response to the rotational force in the first direction, extend linearly with respect to the transmission so as to cause the elbow to flex. The clutch may comprise a cam comprising an annulus, an input side that is adapted to receive an input force, and an output side that is adapted to provide an output force; and a pin and a roller, each located adjacent to the input side of the cam. The cam may be adapted so that movement of the cam in response to the input force causes the pin to push the roller out of contact with the annulus, when a force is applied to the input side of the cam, the pin pushes the roller out of contact with the annulus to allow for movement of the cam. The elbow may comprise a frame adapted to surround the transmission and having an opening for receiving a battery; a socket connector coupled to the elbow, for attaching the elbow to a prosthetic socket; and a position sensor for indicating the rotational movement of the elbow. The screw may be further adapted to receive a rotational force in a second direction from the clutch, and in response to the rotational force in the second direction, retract linearly with respect to the transmission so as to cause the elbow to extend. The socket connector may be coupled to the elbow at a carrying angle. The screw may be a differential roller screw. The elbow may comprise a pivot for the flexion or extension of the elbow. The pivot may be encased in a bushing made of a nonlinear compliant material. The elbow may have a 135 degree range of motion between full flexion and full extension. The elbow may further comprise a shear pin. The elbow may further comprise a first limb portion and a second limb portion coupled together at an elbow joint. A first end of the screw may be coupled to the first limb portion at a bracket. The transmission may be coupled to the second limb portion at a transmission joint. When the screw extends and retracts linearly, the screw may pivot with respect to the bracket. The transmission may pivot with respect to the second limb portion.

In one embodiment, an elbow component for a prosthetic limb may comprise a first limb portion and a second limb portion coupled together at an elbow joint. The transmission may comprise a screw. A first end of the screw may be coupled to the first limb portion at a bracket. The transmission may be coupled to the second limb portion at a transmission joint. The screw and the hinge may be adapted so that when the screw extends linearly in a direction away from the transmission, the screw may apply a force on the bracket that causes the first limb portion to rotate about the elbow joint towards the second limb portion. The screw and the hinge may be adapted so that when the screw retracts linearly in a direction towards the transmission, the screw may apply a force on the bracket that causes the first limb portion to rotate about the elbow joint away from the second limb portion. The transmission and the elbow joint may be adapted so that when the screw extends linearly in a direction away from the transmission, the transmission may rotate about the transmission joint in a first direction. The transmission and the elbow joint may be adapted so that when the screw retracts linearly in a direction towards the transmission, the transmission may rotate about the transmission joint in a second direction opposite to the first direction. When the screw extends and retracts linearly, the screw may pivot with respect to the bracket and the transmission may pivot with respect to the second limb portion. The screw may extend and retract in response to actuation of the transmission. The elbow component may comprise a position sensor to indicate rotational movement of the elbow component. The elbow component may comprise a bushing made of a nonlinear compliant material that encases the transmission pivot; a socket connector coupled to either the first limb portion or the second limb portion; and a frame that surrounds the transmission and is adapted to receive a battery. The screw may be a differential roller screw. The socket connector may be coupled to the first limb portion at a carrying angle. The screw may be coupled to the bracket by a nut.

In one embodiment, a transmission for an elbow joint of a prosthetic limb may comprise a motor, a gear set comprising at least one gear, a non-backdrivable clutch, and a screw, adapted to be housed in a frame pivotally attached to a second portion of the limb. The screw may be adapted to be coupled to a first portion of the limb that is pivotable with respect to the second portion of the limb. The screw may be adapted to receive a rotational force in a first direction from the clutch, and in response to the rotational force in the first direction, extend linearly with respect to the transmission. The screw may be adapted to receive a rotational force in a second direction from the clutch, and in response to the rotational force in the second direction, retract linearly with respect to the transmission. The non-backdrivable clutch may comprise a cam comprising an annulus, an input side that is adapted to receive an input force, and an output side that is adapted to provide an output force; and a pin and a roller, each located adjacent to the input side of the cam. The cam may be adapted so that movement of the cam in response to the input force causes the pin to push the roller out of contact with the annulus, and when a force is applied to the input side of the cam, the pin pushes the roller out of contact with the annulus to allow for movement of the cam. The screw may be a differential roller screw.

The features described above are available in different embodiments of the prosthetic components described, and should not be interpreted to limit or narrow the scope of the claims. The features described herein may additionally be applied in different combinations in different embodiments.

DRAWINGS

While the appended claims set forth the features of the present techniques with particularity, these techniques may be best understood from the following detailed description taken in conjunction with the accompanying drawings of which:

DESCRIPTION

Figure 1:
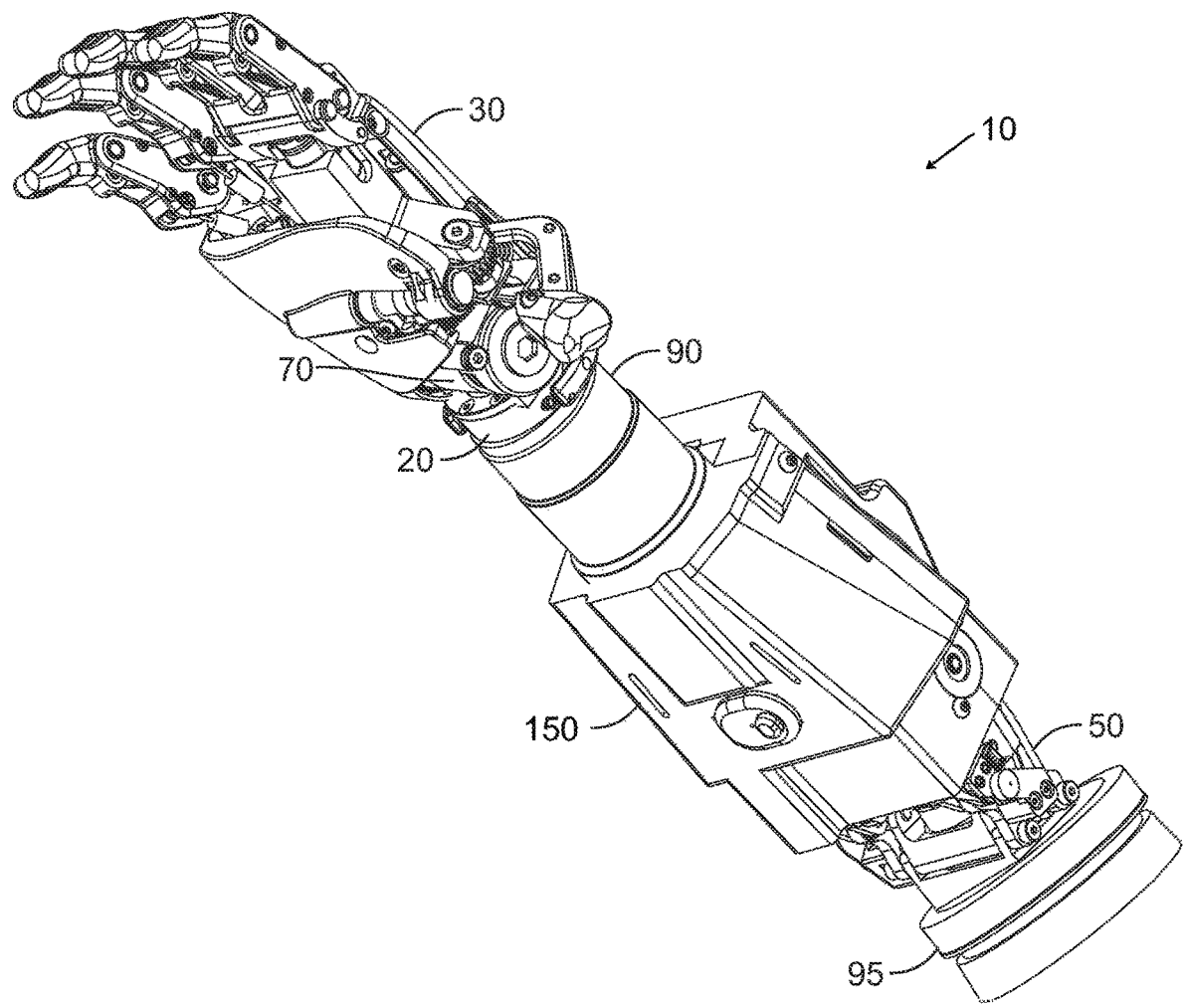
FIG. 1 is a lateral view of a prosthetic limb according to an embodiment.

Turning to the drawings, wherein like reference numerals refer to like elements, the following description is based on embodiments of the claims and should not be taken as limiting the claims with regard to alternative embodiments that are not explicitly described herein.

Embodiments described herein relate to a modular and lightweight prosthetic limb and its modular components. In one embodiment, the prosthetic limb delivers specified torques and motion profiles utilizing its small size, small mass, durable design, and specified axis rotations. The arm maintains different motion profiles, each of which may vary the position, speed, and/or acceleration of its various components. The limb is modular, allowing a user to either use all of the components described herein or swap them out for alternate parts. Different components of the limb may use exterior-rotator motors, which have their rotor on the outside of the stator, as described, for example, in Sensinger, Clark & Schorsch, "Exterior vs. Interior rotors in robotic brushless motors," in IEEE Conference on Robotics and Automation, Shanghai China, 2011, pp. 2764-2770.

FIG. 1 shows a lateral view of a prosthetic limb 10 ("limb 10"). The components of the limb 10 shown in FIG. 1 include a universal coupler 20, a hand 30, a forearm 150, an elbow 50, a wrist flexor 70, and a wrist rotator 90. The limb 10 further includes a socket connector 95 that connects to the distal end of a user's prosthetic socket (not shown). The hand 30, the wrist flexor 70, the wrist rotator 90, and the elbow 50 are modular, allowing clinicians to provide an amputee user with only the components he or she needs based on his or her level of amputation. For example, a below-elbow amputee, whose arm still has the elbow, would not need the elbow 50 component. Each modular component is connected by a CAN bus communication standard for prosthetic arms and a universal coupler 20, allowing users to swap different hands for different applications such as an electric hook, a lightweight hand, or a more powerful hand. The universal coupler 20 allows a user to attach, detach, spin, and lock in a component of the arm. One possible embodiment of the universal coupler 20 is described in Sutton, Clawson, et al, "Towards a universal coupler design for modern powered prostheses," Myoelectric Controls Symposium, Fredericton, Canada, 2011.

In one embodiment, the limb 10 may be covered by a cosmesis to provide protection from liquids and dirt, and to result in appearing as a natural limb.

Figure 3:
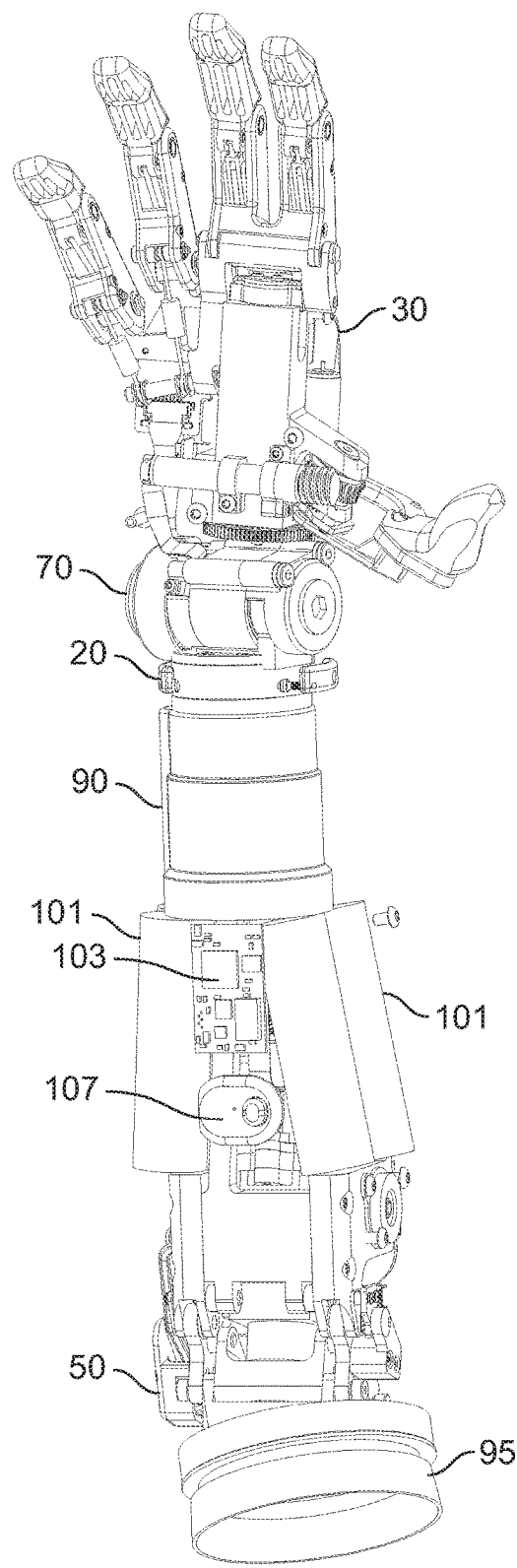
FIG. 3 is a cut-away anterior view of the prosthetic limb, according to an embodiment.
Figure 4:
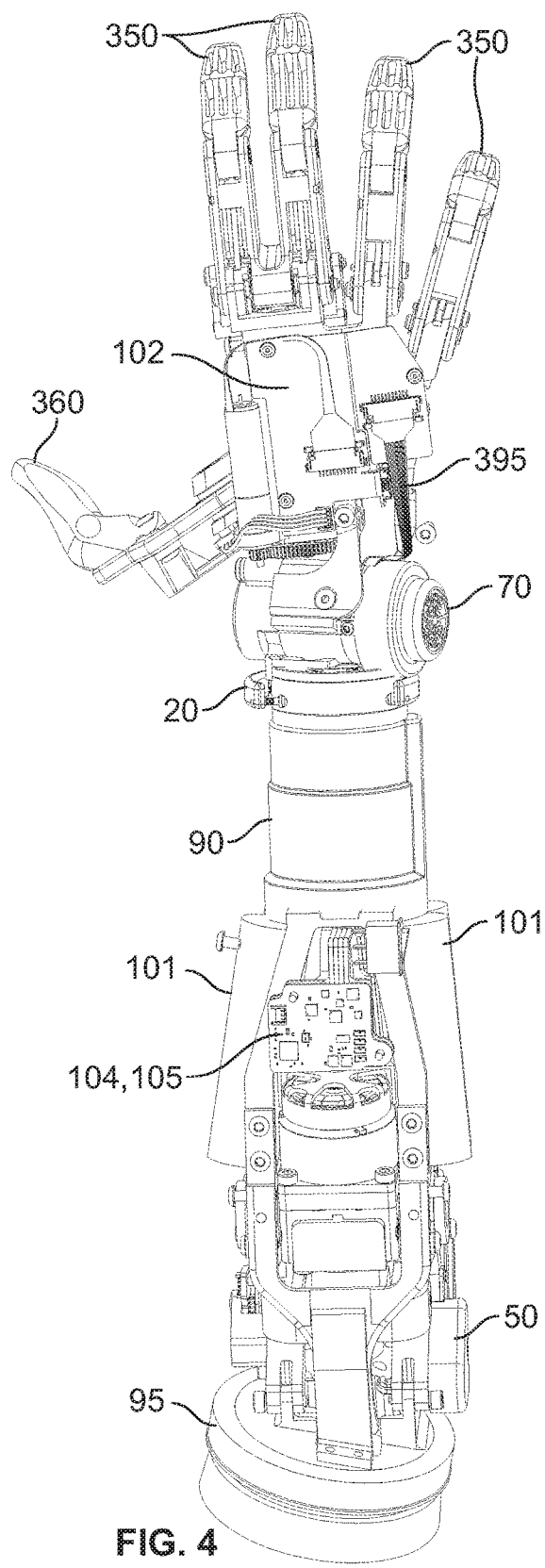
FIG. 4 is a cut away posterior view of the prosthetic limb, according to an embodiment.

FIG. 3 shows a cut-away anterior view of the limb 10 and FIG. 4 shows a cut-away posterior view of the limb 10. Four batteries 101 that provide power to the limb 10 are housed in a forearm 150. In one embodiment, each battery 101 is a 14.8V Tenergy Li-Ion 18500 Cylindrical 3.7V 1400 mAh with tabs from All-Battery. In other embodiments, the batteries 101 could be housed externally to the limb 10, for instance on a user's belt. As shown in FIG. 4, a master controller 102 is housed on top of the hand 30.

In one embodiment, the master controller 102 is housed in the forearm 150 and controls the movement of fingers 350, a thumb 360, the wrist flexor 70, the wrist rotator 90, and the elbow 50. The master controller 102 may be programmed with a pattern recognition module, a direct control module, or another module known in the art in order to cause different components of the limb 10 to move. In one embodiment, the master controller 102 is programmed with a control module, modified from small motor controller software obtained under license from the Johns Hopkins University Applied Physics Laboratory (Laurel, Md.) to allow CAN communication. The master controller 102 may record user signals from sensors 26 coupled to a user's socket 25. The sensors 26 may be EMG sensors or other appropriate sensors. The master microcontroller 102 uses a 4-wire CAN bus to communicate the movements of the components of the limb 10.

A flexible circuit 395 is coupled to the master controller 102 for communication to and from the master controller 102. Where the limb 10 makes use of pattern recognition control using EMG signals, the master controller 102 communicates with the sensors 26 in the user's socket 25 (not shown) to train the pattern recognition control module and to operate the limb 10. A training switch 107 switches the limb 10 between a training mode, in which information collected from the sensors 26 train the pattern recognition module, and an operating mode, in which information collected from the sensors 26 are used by the master controller 102 to move different components of the limb 10, including the elbow 50, the wrist rotator 90, the wrist flexor 70, the fingers 350, and the thumb 360. Wire connectors for power, ground, and communication signals (not shown) extend from the proximal end of the socket connector 95 for connection with the appropriate electrodes at the user's socket 25.

As shown in FIG. 3, in one embodiment the forearm 150 also may house a secondary controller 103. In one embodiment, the secondary controller 103 may control the movement of the elbow 50 and the wrist rotator 90. Such a configuration can be useful when the universal coupler 20 is released and the master controller 120 is separated, along with the wrist flexor 70 and the hand 30, from the rest of the limb 10. An elbow board 104 controls an exterior-rotor motor 510 and a rotator board 105 controls an exterior-rotor motor 910.

Hand.

Figure 5:
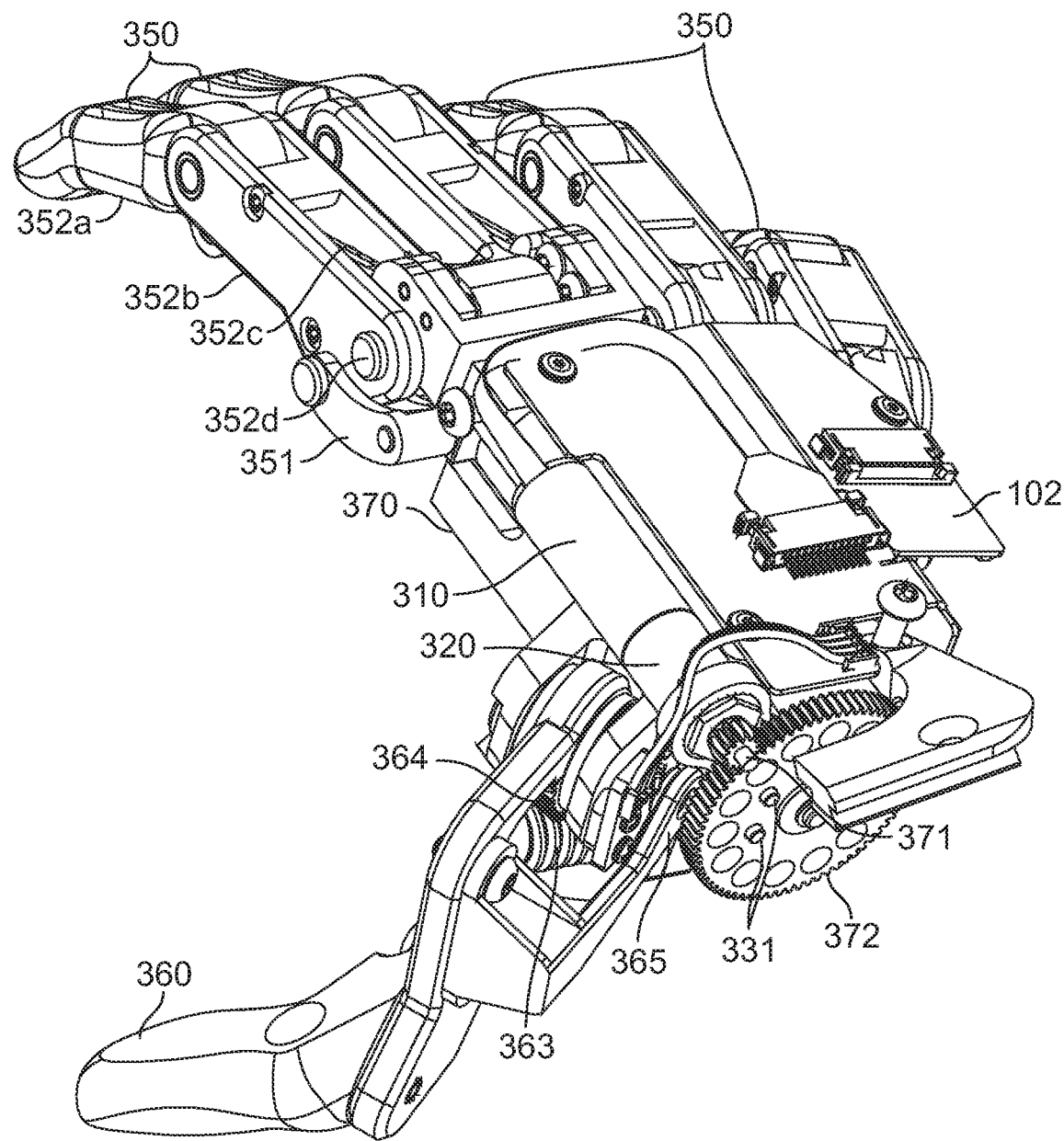
FIG. 5 is a posterior view of a hand of the prosthetic limb, according to an embodiment.

As shown in FIG. 5, the hand 30 is a modular component that comprises an endoskeleton 370, the fingers 350, the thumb 360, hand-motor motor-amplifiers (not shown), and the master controller 102. The endoskeleton 370 is fastened to the output of the wrist flexor 70. In one embodiment, the endoskeleton 370 is made of aluminum or another suitable lightweight material. The endoskeleton 370 supports the fingers 350 and the thumb 360. The endoskeleton 370 also houses the hand-motor motor-amplifiers and a hand microcontroller (not shown), which are embedded in the master controller 102. The hand 30 further comprises a rotor motor 310, a planetary gear transmission 320, a non-backdrivable clutch 330, a differential roller screw 340, and a finger linkage 355. In one embodiment, the rotor motor 310 is a brushless interior rotor motor and is coupled to the planetary gear transmission 320.

Figure 6:
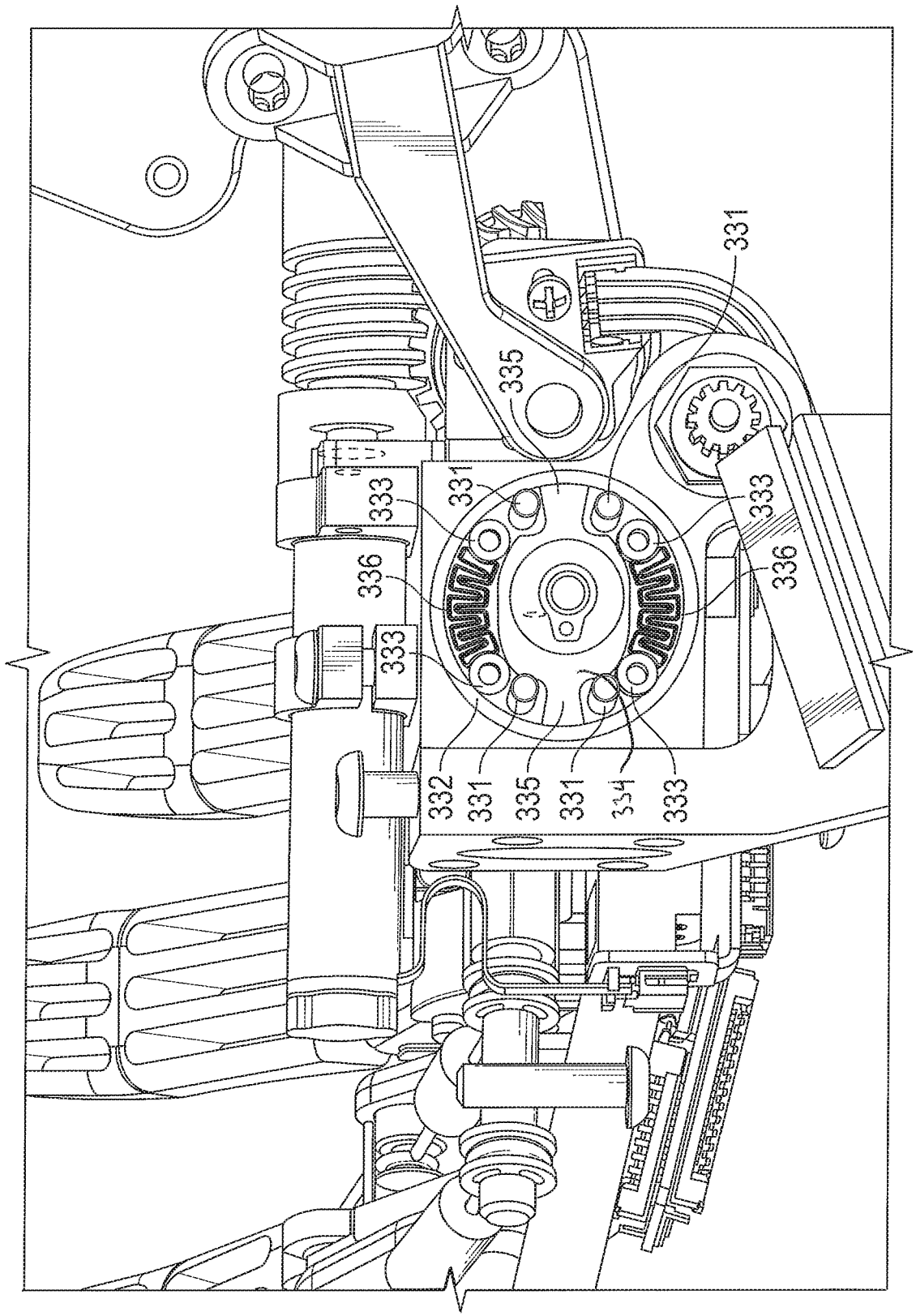
FIG. 6 is a proximal view of the hand of the prosthetic limb, showing a possible implementation of a non-backdrivable clutch.

The rotor motor 310 and the planetary gear transmission 320 actuate a pinion gear 371, which actuates a finger gear 372. The finger gear 372 is connected to pins 331, which extend into a clutch 330 to drive the clutch 330. FIG. 6 shows the clutch 330 as a non-backdrivable clutch located at the proximate end of the hand 30. The clutch 330 in this embodiment comprises an annulus 332, rollers 333, an output cam 334, and springs 336. The springs 336 ensure that the rollers 333 are in contact with the annulus 332 when the clutch 330 is not being driven. As a finger gear 372 turns to actuate the clutch 330, the pins 331 push the rollers 333 out of contact with the annulus 332, allowing the output cam 334 to turn. The pins 331 also engage protrusions 335 on the output cam 334. Motion of the output cam 334 occurs when the pins 331 push the rollers 333 out of contact with the annulus 332 before they engage the protrusions 335 on the output cam 334. If movement is attempted from the output side of the clutch 330 without pushing the rollers 333 out of the way, the jam angle between the grounded annulus 332, the rollers 333, and the output cam 334 prevents motion from occurring. The annulus 332 includes a mechanical fuse (not shown) to prevent excessive torque applied to the fingers 350 from damaging the rotor motor 310. For instance, if the user falls on the hand 30, the mechanical fuse fails and may be replaced with relative ease.

Figure 7:
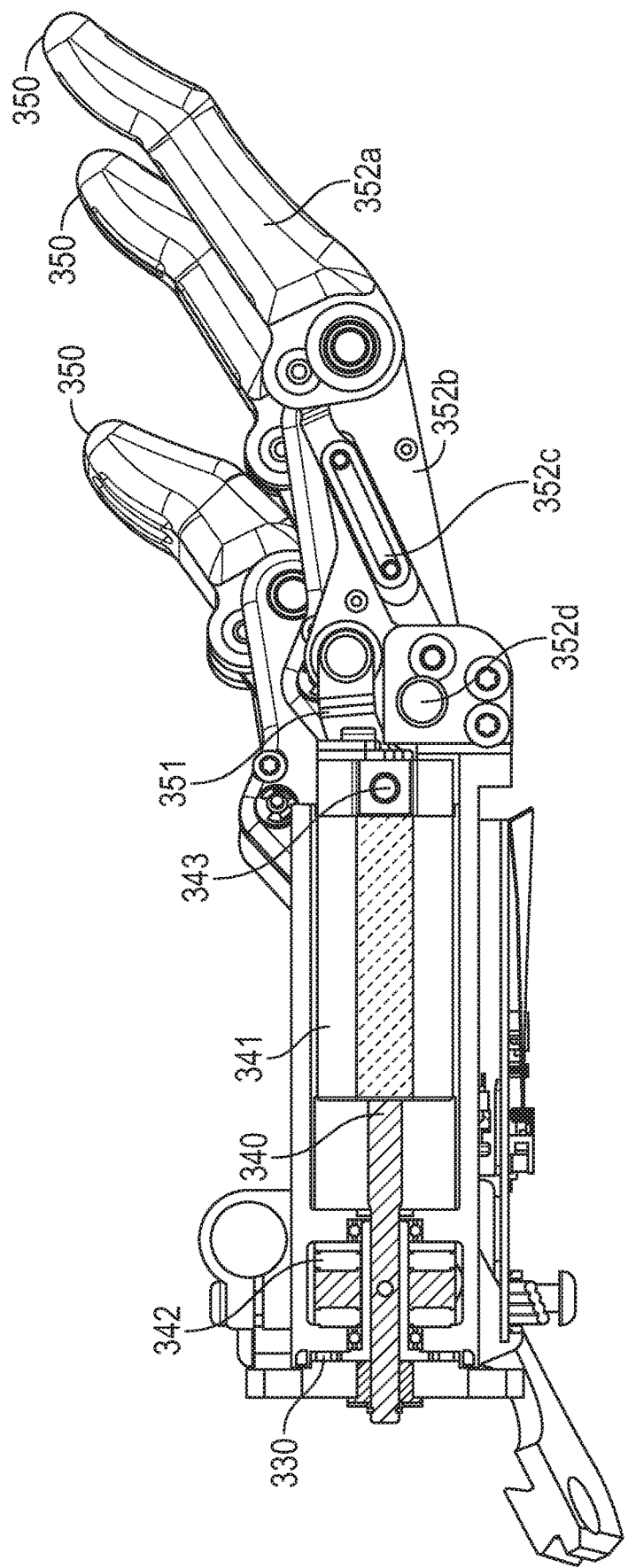
FIG. 7 is a cross-section lateral view of the hand of the prosthetic limb, according to an embodiment.

FIG. 7 is a cross-section lateral view of the hand 30. The differential roller screw 340 is housed in a casing 341 that prevents bending moments upon the differential roller screw 340. A thrust bearing 342 prevents axial loads from the differential roller screw 340 from being transmitted to the clutch 330. The differential roller screw 340 is affixed via a pivot 343 to a linkage connector 351, which in turn connects to a linkage 352 of the fingers 350. The linkage 352 comprises a first link 352a, a second link 352b, a third link 352c, and a link 352d to ground, as shown in FIG. 5. The rotational motion of the output cam 334 causes the differential roller screw 340 to thread through the casing 341, causing a roller screw nut 343 to move distally or proximally in response to motion of output cam 334. The linkage connector 351 moves in response to movement from the roller screw nut 343, which in turn activates the linkage 352, causing the fingers 350 to flex and extend.

Figure 8:
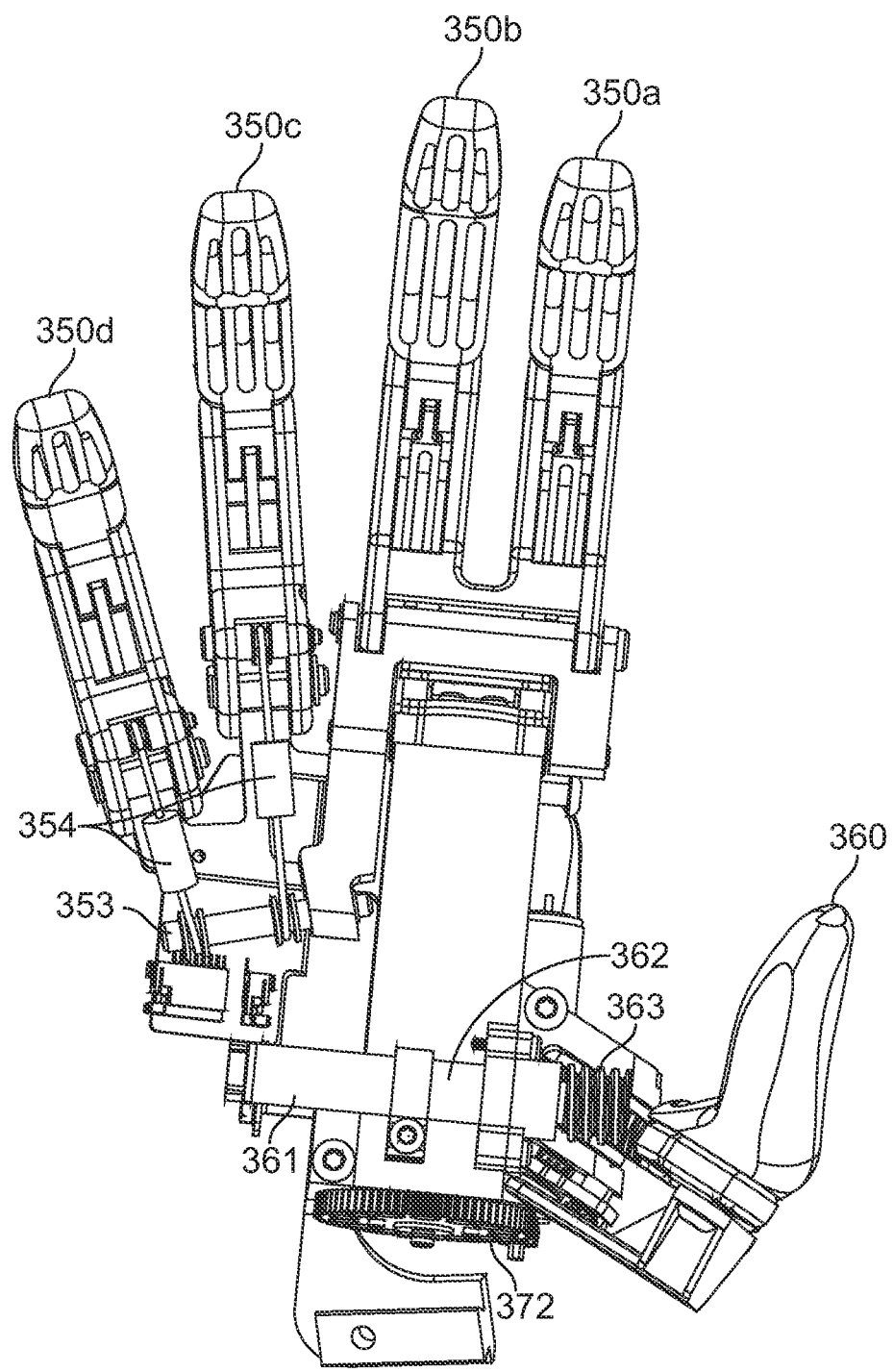
FIG. 8 is an anterior view of the hand of the prosthetic limb, according to an embodiment.

FIG. 8 shows an anterior view of the hand 30. A side arm 353 projects from the differential roller screw 340 to transmit motion to a ring finger 350c and a pinky finger 350d via lateral finger springs 354. The linkage 352 transmits motion from the differential roller screw 340 to the fingers 350 without creating a bending moment on the differential roller screw 340. FIG. 8 also shows the fingers 350. Each finger 350a, 350b, 350c, and 350d employs the linkage 352—a four-bar linkage in the illustrated embodiment. The linkage 352 couples flexion of the metacarpophalangeal joint ("MCP") to flexion of the proximal interphalangeal joint ("PIP") joint. This four-bar linkage geometry is optimized to provide maximal pinch-force to motor torque ratio, within spatial and mechanical constraints, while generating motion that is anatomically natural. Linkages for each finger 350 are shown at FIG. 5, where the linkage 352 for the index finger 350a is labeled. The link connecting the frame to the distal phalange in each finger is designed with longitudinal compliance, resulting in approximately 5 degrees of compliance at the PIP joint for the index finger 350a and the middle finger 350b. In one embodiment, the proximal phalanges of the index finger 350a and the middle finger 350b are fused together for rigidity. The ring finger 350c and the pinky finger 350d are each independently hinged, and coupled via compliant springs 354 to the side arm 353. Having the ring finger 350c and the pinky finger 350d independently hinged allows for them to move with the index and middle fingers 350a and 350b, and to generate a conformal grasp by the hand 30.

Thumb.

Figure 9:
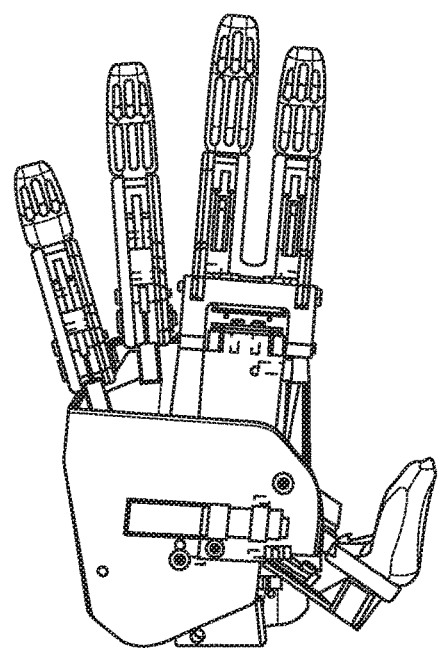
FIG. 9 shows the hand of the prosthetic limb in a relaxed posture, according to an embodiment.
Figure 10:
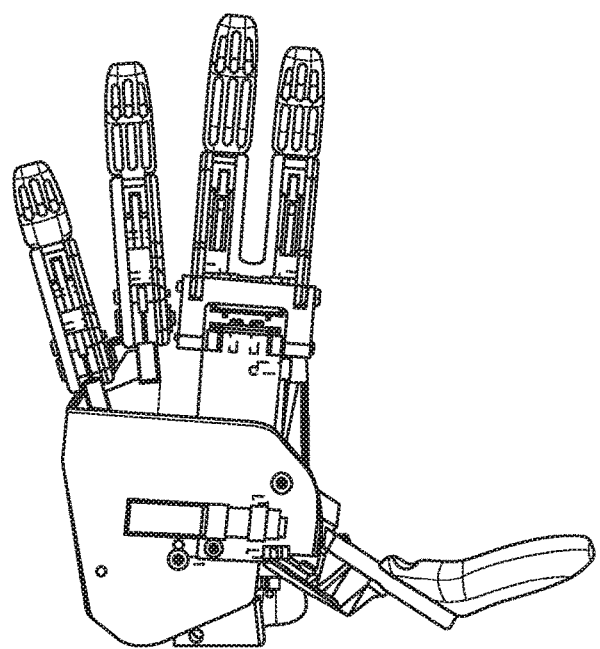
FIG. 10 shows the hand of the prosthetic limb in a palm-flat posture, according to an embodiment.
Figure 11:
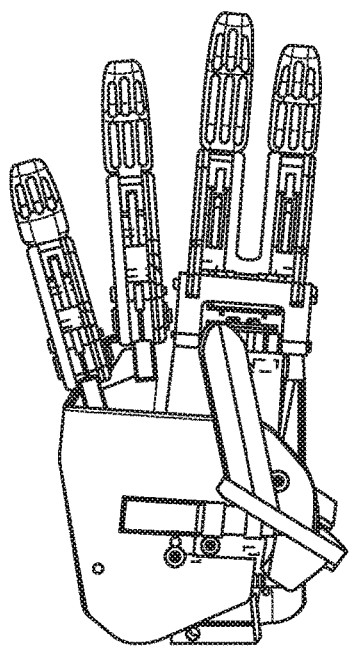
FIG. 11 shows the hand of the prosthetic limb in a chuck grip posture, according to an embodiment.
Figure 12:
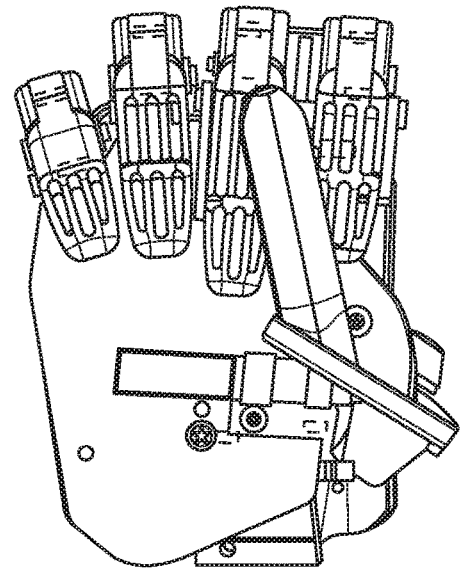
FIG. 12 shows the hand of the prosthetic limb in a cylindrical grip posture, according to an embodiment.

In one embodiment, the thumb 360 comprises its own rotor motor 361 coupled to a planetary gear 362. According to an embodiment, the thumb 360 is independently powered from the finger 350 and is driven by the rotor motor 361 and planetary gear 362 so as to act independently of the fingers 350. Having an independent thumb 360 increases the stability of the gripping ability of the hand 30. The thumb 360 has a single degree of freedom. In one embodiment, the rotor motor 361 is a brushless interior rotor motor, model EC10 from Maxon Precision Motors, Inc. (Fall River, Mass.), which is coupled to the planetary gear transmission 362 offered by the same company. Movement is transmitted from the planetary gear transmission 362 to the thumb 360 via a worm pinion 363 that interfaces with a worm gear 364. In one embodiment, the worm gear 364 is a custom, off-axis helical worm gear, made of brass. In one embodiment, shown in FIG. 5, the worm gear 364 is positioned posterior to the worm pinion 363. The worm gear 364 converts motion from the worm pinion 363 to the rotation axis of the thumb 360. The axis of the thumb 360 is positioned such that the thumb 360 may provide multiple different hand postures with a single degree of freedom. These postures include relaxed (shown at FIG. 9), palm-flat (shown at FIG. 10) chuck grip (shown at FIG. 11), and cylindrical grip (shown at FIG. 12). To fit the rotor motor 361 and the thumb transmission (including the planetary gear 362 and the worm pinion 363) within the hand 30 profile, the axis of the worm pinion 363 is skewed by approximately 20 degrees. The tooth profile of the worm gear 364 allows for proper meshing with the skewed position of the worm pinion 363. A position sensor 365 senses the position of the thumb 360, and information from the position sensor 365 is used by the master controller 102 for position control of the thumb 360. In one embodiment, the position sensor 365 is a magnetic hall-effect sensor, shown in FIG. 5.

Wrist.

In an embodiment, the wrist of the limb 10 has two degrees of freedom: rotation from the wrist rotator 90 and flexion from the wrist flexor 70. Each of the wrist rotator 90 and the wrist flexor 70 is a wrist component. The wrist rotator 90 comprises an exterior-rotor motor 910, a planetary gear transmission 920, a non-backdrivable clutch 930, and a cycloid transmission 940. In one embodiment, shown in FIGS. 1-4, the wrist rotator 90 has an outer diameter of 20 mm and a length of 13 mm. In one embodiment, insulation material is made of Paralyne with an insulation thickness of 0.0508 nm. The wrist rotator may utilize a supply voltage of 14.8V and a supply current of 4 A from batteries 101, and include WYE termination and a net fill factor of 65%. Seals may be applied to the wrist flexor 70 and the wrist rotator 90 to make them water-resistant.

The wrist rotator 90 is powered by the exterior-rotor motor 910, which in one embodiment is a DC brushless motor. Magnets are placed at the ends of each tooth, radial to the center of the motor's stator. In one embodiment, 14 magnets are placed distally around the center of the stator. The magnets are arranged in an alternating pole arrangement, where each magnet's pole is opposite to its neighbor. Each stator tooth is wrapped with three-phase, single span windings resulting in three sets of wires looped around the stator. The winding pattern is AacCBbaACcbB, where capital letters denote clockwise winding and lower-case letters denote counter-clockwise winding, and A, B, and C denote the three phases.

In one embodiment, the exterior-rotator motor 910 is controlled by the master controller 102. In other embodiments, where the master controller 102 is not available in the hand 30, the exterior-rotator motor 910 may be controlled by the secondary controller 103. The control module on either the master controller 102 or the secondary controller 103 times when current should run through each motor winding of the exterior-rotator motor 910 and sends a signal to FETs to drive the exterior-rotator motor 910.

Figure 13:
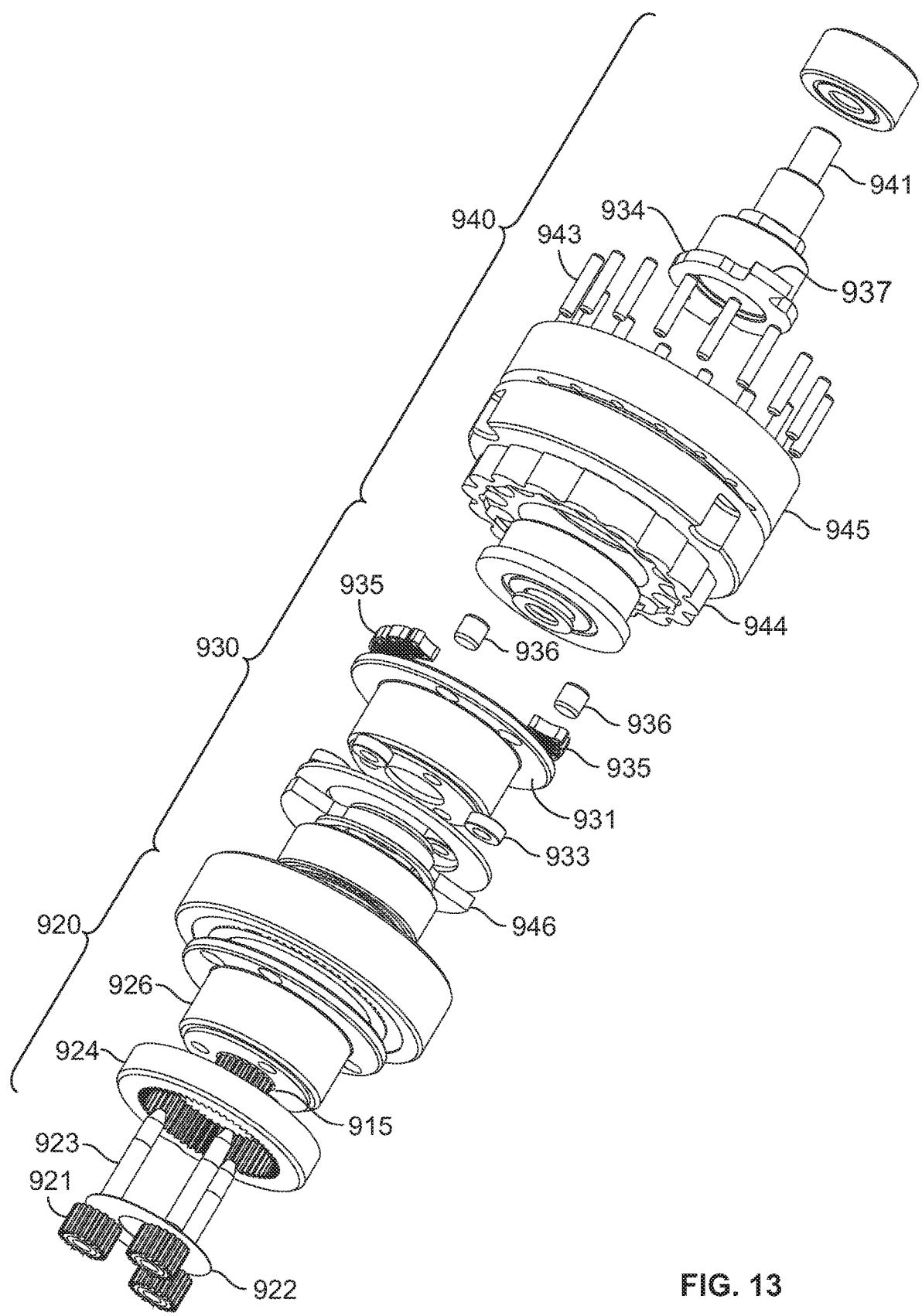
FIG. 13 is an exploded view of the planetary gear transmission, non-backdrivable clutch, and cycloid transmission components of the wrist rotator of the prosthetic limb, according to an embodiment.

The exterior-rotator motor 910 is connected to a planetary gear transmission 920, shown in FIG. 13. The planetary gear transmission 920 comprises a grounded annulus 924, a sun gear (input) 925 fastened to the motor output, planetary gears 921, and a carrier plate (output) 926. In one embodiment, the planetary gear transmission 920 is a modified 1-stage planetary gear modified from a stock MicroMo gear (16/7 246:1). In other embodiments, the planetary gear transmission 920 may comprise a 2-stage planetary gear.

The output of planetary gear transmission 920 is coupled to a non-backdrivable clutch 930, also shown at FIG. 13. In one embodiment, the non-backdrivable clutch 930 allows motion from the planetary gear transmission 920 to be transmitted to the non-backdrivable clutch 930 output in either direction, clockwise or counter-clockwise, but inherently prevents any additional movement from the output of the non-backdrivable clutch 930 to be transmitted to the input of the cycloid transmission 940, thus allowing the actuation unit (i.e., the planetary gear transmission 920, the non-backdrivable clutch 930, and the cycloid transmission 940) to maintain a position without requiring constant power consumption from the motor, as described further in M. Controzzi, C. Cipriani, M. C. Carrozza. Miniaturized non-back-drivable mechanism for robotic applications, Mechanism and Machine Theory, Elsevier, vol. 45, no. 10, pp. 1395-1406, 2010. This locking feature allows a user to carry a heavy object, such as a grocery bag, without the batteries 101 needing to supply power to the motors to keep the object lifter. As a result, the wrist rotator 90 is capable of passively holding more force than it can actively generate.

As shown in FIG. 13, the non-backdrivable clutch 930 comprises an input plate 931, a grounded annulus 932 (encapsulating the clutch 930, and not shown), four rollers 933, an output cam 934, and two springs 935 that ensure the rollers 933 are in contact with the ground. Pins 936 on the input plate 931 push the rollers 933 out of contact with the grounded annulus 932. The pins 936 on the input plate 931 also engage protrusions 937 on the output cam 934. Motion of the non-backdrivable clutch 930 occurs when the pins 936 push rollers 933 out of contact with the grounded annulus 932 before the pins 936 engage the protrusions 937 on output cam 934. If movement is attempted from the output side of the non-backdrivable clutch 930 without pushing the rollers 933 out of the way, the jam angle between the grounded annulus 932, the rollers 933, and the output cam 934 prevents motion of the non-backdrivable clutch 930 from occurring.

Figure 14:
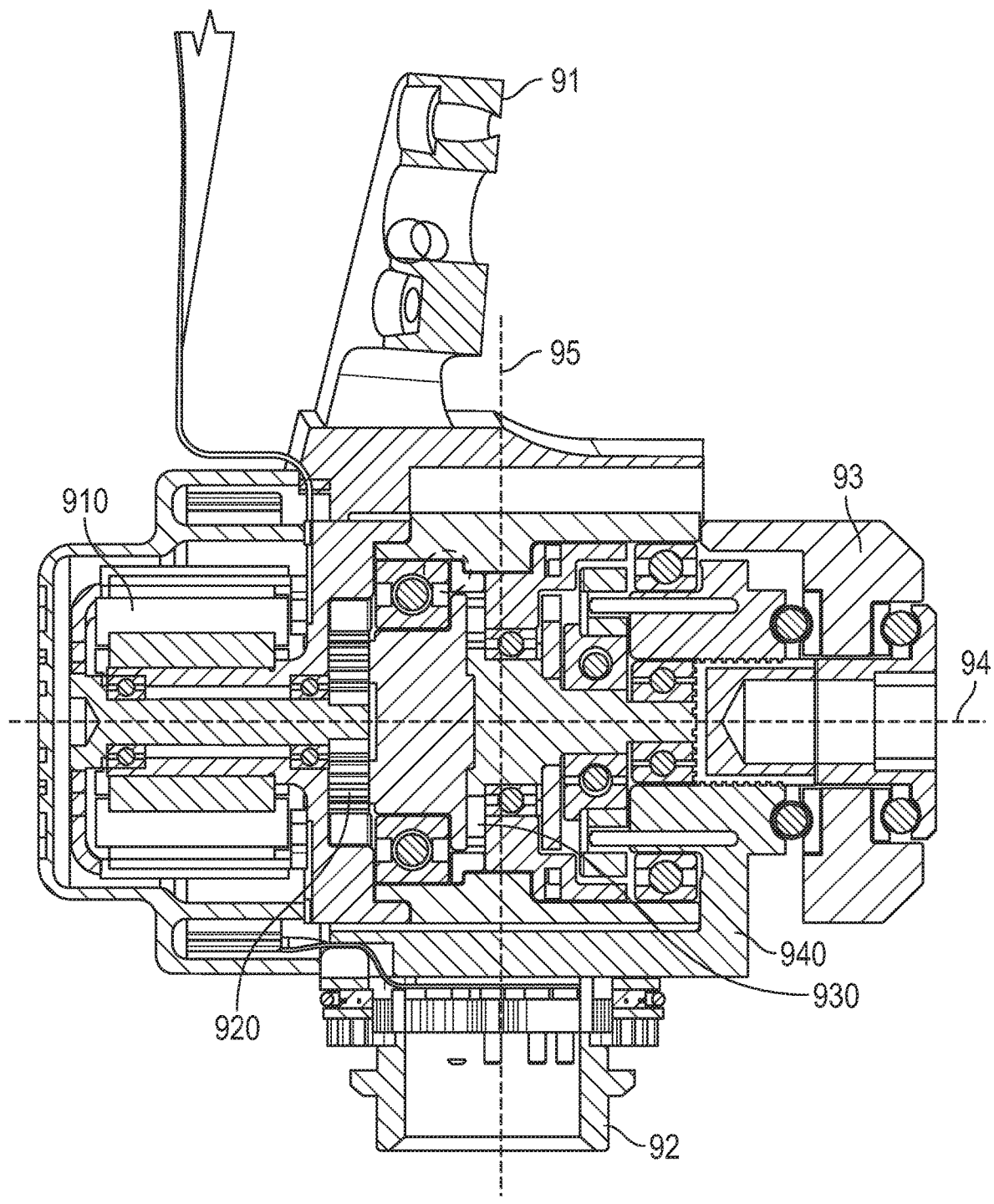
FIG. 14 is a cross-section view of the wrist rotator of the prosthetic limb, according to an embodiment.

Still with respect to FIG. 13, the output of the non-backdrivable clutch 930 is connected to a cycloid transmission 940, as described further in references J. W. Sensinger, "Efficiency of High-Sensitivity Gear Trains, Such as Cycloid Drives," J. Mech. Des. 135(7), 071006 (2013) (9 pages); Del Castillo, J. M., 2002, "The Analytical Expression of the Efficiency of Planetary. Gear Trains," Mech. Mach. Theory, 37(2), pp. 197-214, 2002; and J. W. Sensinger, Unified Approach to Cycloid Drive Profile, Stress, and Efficiency Operation," J. Mech. Des. 132(2), 024503 (2010) (5 pages). The cycloid transmission 940 comprises a grounded annulus (not shown) that houses a set of freely spinning rollers 943, an eccentric input cam 941, a cycloid disk 944, and an output carrier plate 945. In one embodiment, parameters of the cycloid transmission 940 may be optimized so that the torque ratio of the cycloid transmission 940 is 16:1 and its outer diameter is 23 mm. As a result of these constraints, the input eccentricity of the cycloid transmission 940 is 0.57 mm, its roller diameter is 1 mm, and its roller offset diameter is 20 mm. These parameters are optimized to provide minimum radial loading while maintaining a design without undercutting the gear-tooth profile. The cycloid disk 944 profile may be determined using the methods set out in reference J. W. Sensinger, Unified Approach to Cycloid Drive Profile, Stress, and Efficiency Operation," J. Mech. Des. 132(2), 024503 (2010) (5 pages). A counter-weight 946 is also shown in FIG. 13. In an embodiment, the counter-weight 946 is attached to the eccentric input shaft 947 at 1800 out of phase with the cycloid disk 944, so as to cancel out oscillatory vibrations. FIG. 14 displays a cross section view of the transmission components of the wrist rotator 90. It should be understood that although one embodiment of planetary gear transmission 920, non-backdrivable clutch 930, and cycloid transmission 940 is detailed here, other embodiments would be apparent to one of ordinary skill in the art. As shown in FIG. 14, the plate 91 may be configured to be coupled to the frame of the hand 30. Housing 93 provides a cover to the wrist rotator 90 and may be made of plastic or another suitable material. A connector 92 may be configured to connect to the output of the wrist flexor 70, so as to transfer the flexion/extension motion produced by the wrist flexor 70 through the wrist rotator 90 and to the hand 30, along a flexor axis 95, shown in FIG. 14. Actuation of the transmission of the wrist rotator 90 causes the wrist rotator 90 to rotate around a rotator axis 94 along the a cycloid output 750 (shown in FIG. 2).

In one embodiment, contribution of increasing the torque was balanced between the torque ratios of the planetary gear transmission 920 (3.71:1) and the cycloid transmission 940 (16:1) using the known efficiency of both mechanisms as set out in J. W. Sensinger, "Efficiency of High-Sensitivity Gear Trains, Such as Cycloid Drives," J. Mech. Des. 135(7), 071006 (2013) (9 pages) and Del Castillo, J. M., 2002, "The Analytical Expression of the Efficiency of Planetary. Gear Trains," Mech. Mach. Theory, 37(2), pp. 197-214, 2002, in order to maximize the total torque produced by wrist rotator 90 while ensuring a reasonably low stress on the components of the wrist rotator 90.

The distal end of the wrist rotator 90 includes a bulls-eye pattern of four copper ring interfaces, for transmitting four signals across the axis of rotation of the wrist rotator 90. In one embodiment, one of the interfaces transmits power, two of the interfaces transmit communication signals, and one of the interfaces acts as an electrical ground. The proximal end of the wrist flexor 70 includes multiple conductive pins. When the wrist flexor 70 is coupled to the wrist rotator 90, and the limb 10 is in training mode or operating mode, the multiple conductive pins provide power from the batteries 101 to the wrist flexor 70 and the hand 30. The concentric pattern of copper ring interfaces, and their connection to the spring-loaded pins, allow for continuous operation of the limb 10 while the wrist rotator 90 is rotating. The distal portion of the wrist rotator 90 is the proximal side of the universal coupler 20, which allows the wrist to be interchanged with a variety of hand units. In other embodiment, a battery powering hand 30 could be housed in hand 30.

Figure 2:
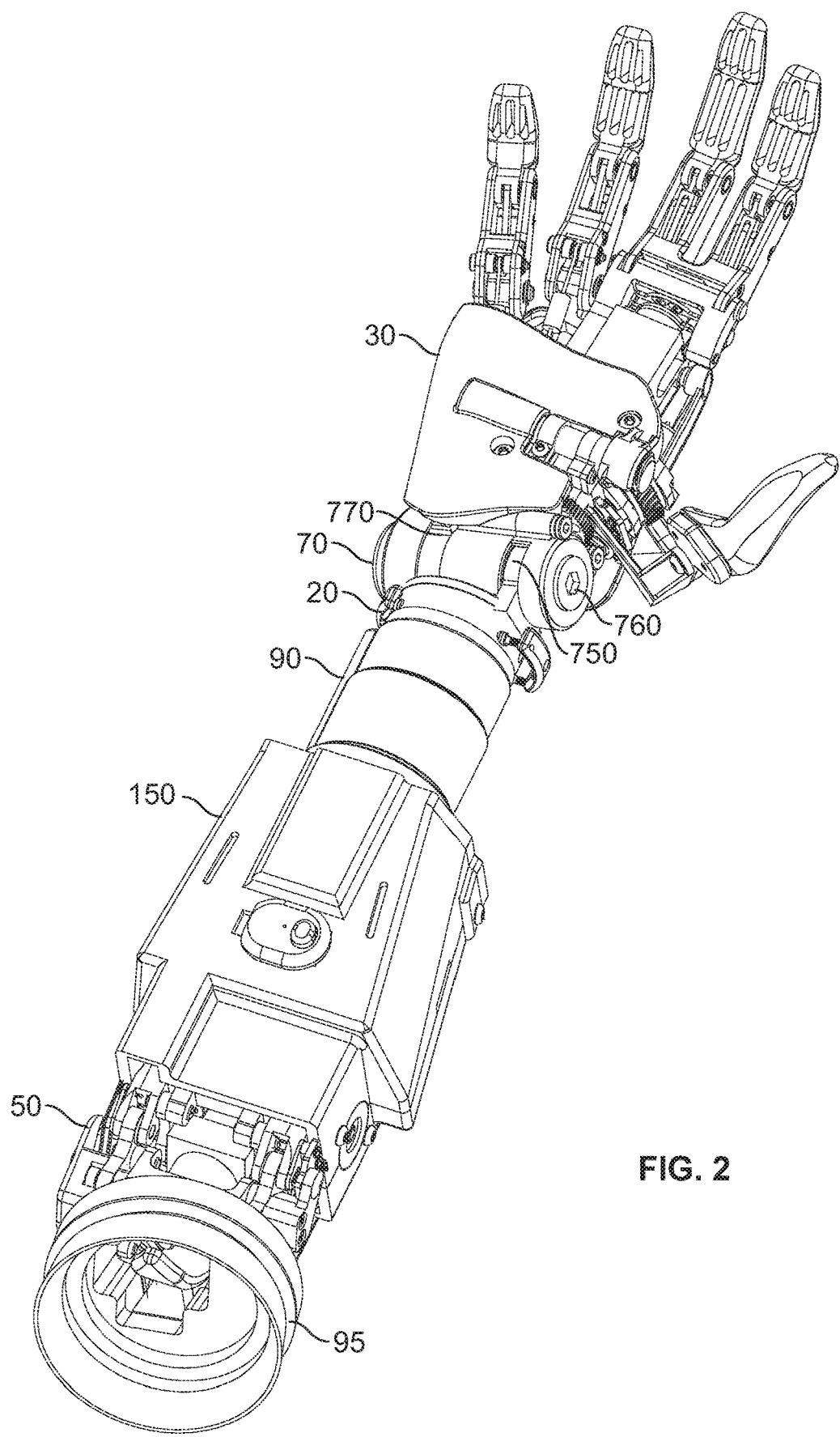
FIG. 2 is an anterior view of a prosthetic limb, according to an embodiment.

Wrist flexor. In an embodiment, the wrist flexor 70 utilizes the same drivetrain design used in the wrist rotator 90, described herein, including the exterior-rotor motor 910, the planetary gear transmission 920, the non-backdrivable clutch 930, and the cycloid transmission 940. The wrist flexor 70 uses a flexible circuit (not shown) to pass electrical signals, including signals to and from the master controller 102 and the secondary controller 103, across its axis of rotation. FIG. 2 shows an anterior view of the limb 10, including a view of the wrist flexor 70. The wrist flexor 70 has a range of motion limited by a mechanical stop 770. The wrist flexor 70 is of modular design and is coupled to the wrist rotator 90 by the universal coupler 20. The proximal portion of the wrist flexor 70 is the distal portion of the universal coupler 20. The wrist flexor 70 includes a shear pin (not shown) that breaks at a specified excessive torque, which limits damage to the wrist flexor 70 if the user falls and lands on the wrist flexor 70 or if the wrist flexor 70 is the subject of other accidental force.

The rotation axis of the wrist flexor 70 actuates primarily in the direction of flexion and extension. The axis location is skewed by 10-30 degrees to provide radial/ulnar deviation in addition to the primary flexion/extension directions of motion. This results a movement known as a dart-thrower motion that has been found to be the most common movement in activities of daily living. The wrist flexor 70 and the wrist rotator 90 could be coupled to the hand 30, or to another commercially available prosthetic hand, such as the Transcarpal Hand offered by Ottobock (Duderstadt, Germany).

Elbow. In one embodiment, the elbow 50 is a modular unit that provides flexion and extension about the elbow axis. The elbow 50 generates movement of the forearm 150 in response to a command of the user.

Figure 15:
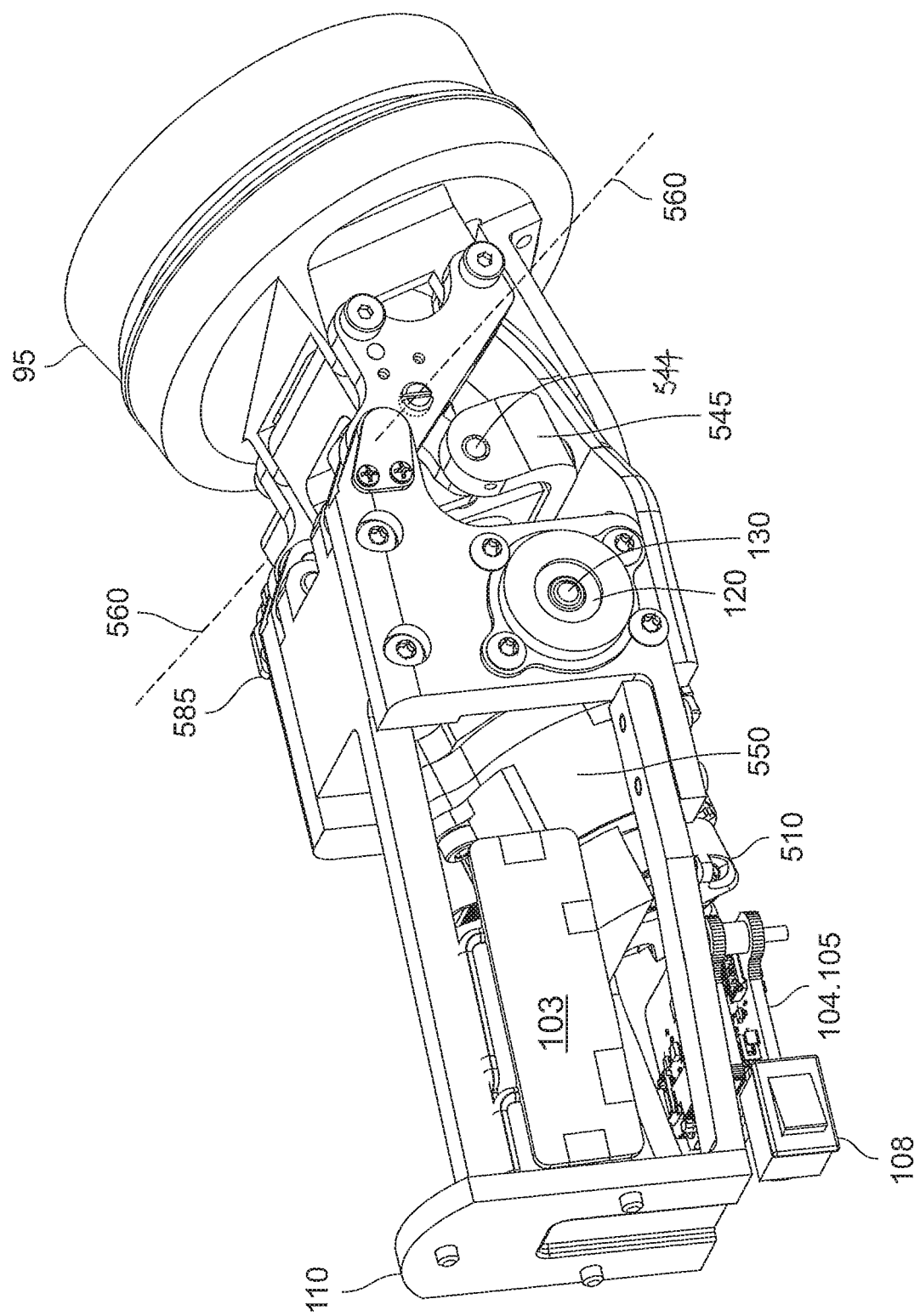
FIG. 15 is a lateral view of the elbow of the prosthetic limb, according to an embodiment.

FIG. 15 shows a lateral view of the elbow 50. In one embodiment, the elbow 50 is connected to the frame 110, which has openings for the batteries 101 (not shown in FIG. 15). An on/off switch 108 for the limb 10 is coupled to the frame 110. The frame 110 surrounds a transmission housing 550 and supports an elbow hinge joint 130 and a bushing 120. A position sensor 585 indicates rotational movement of elbow 50. In one embodiment, the position sensor 585 is a magnetic hall-effect sensor. The axis of rotation of the elbow 50 is shown by the line 560. The distal end of the elbow 50 is coupled to the socket connector 95. The flexion axis is offset ventrally to the limb center. This allows additional components to be packaged in the elbow space, but leaves a gap when the elbow is fully flexed. This gap may be covered by a compliant covering, such as rubber or fabric.

Figure 16:
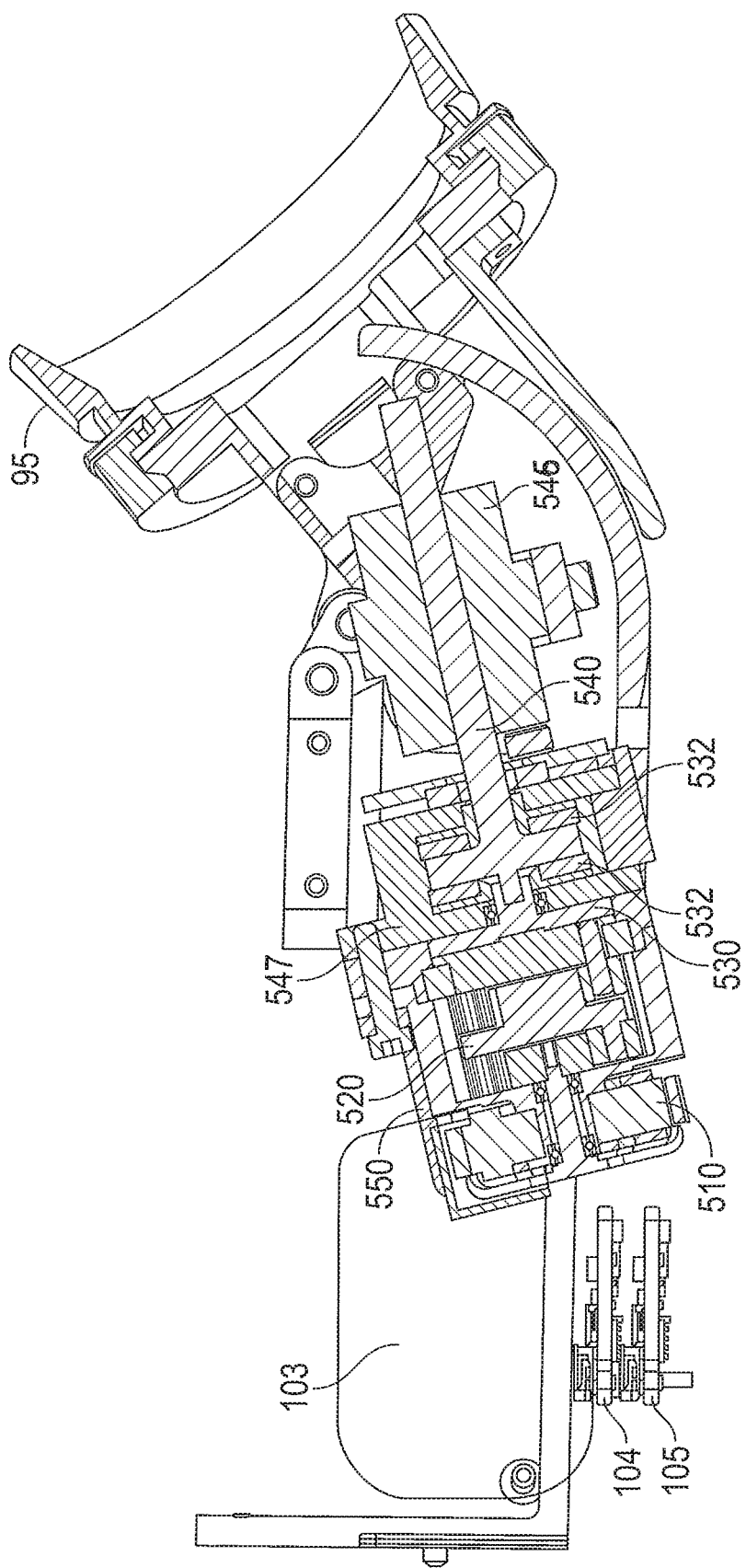
FIG. 16 is a cross-section view of the elbow of the prosthetic limb, according to an embodiment.

FIG. 16 shows a cross-section view of the elbow 50. The elbow 50 comprises an exterior-rotor motor 510. In an embodiment, the exterior-rotor motor is of the same design as the exterior-rotor motor used in the wrist rotator 90. The elbow 50 further comprises a planetary gear transmission 520, which, as shown in FIG. 16, is a two-stage planetary transmission. In an embodiment, the planetary gear transmission 520 is modified from a stock gear offered by MicroMo (Clearwater, Fla.) that increases output torque while reducing speed. The elbow 50 further comprises a non-backdrivable clutch 530 coupled to a differential roller screw 540. In general, differential roller screws such as the differential roller screw 540 are useful to convert rotary motion to linear motion, as it has high efficiency (86%) similar to a ball screw, yet can withstand high axial forces, similar to lead screws, that result from the loads experienced by the arm. In one embodiment, the differential roller screw 540 converts the rotary motion of the non-backdrivable clutch 530 to linear motion. In one embodiment, a non-backdrivable differential roller screw may be used. A thrust housing 547 pushes against the differential roller screw 540 when the differential roller screw 540 actuates to flex the elbow 50. The elbow 50 may include one or more thrust bearings 532, for example two as shown, within the thrust housing 547 and in contact with an end of the differential roller screw 540.

Figure 17:
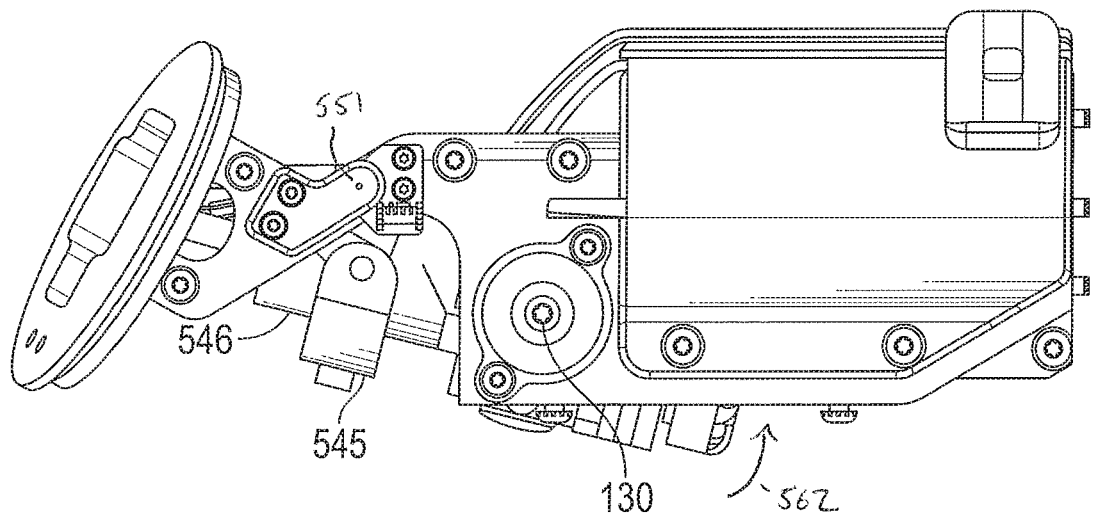
FIG. 17 shows the elbow of the prosthetic limb in an extended position, according to an embodiment.
Figure 18:
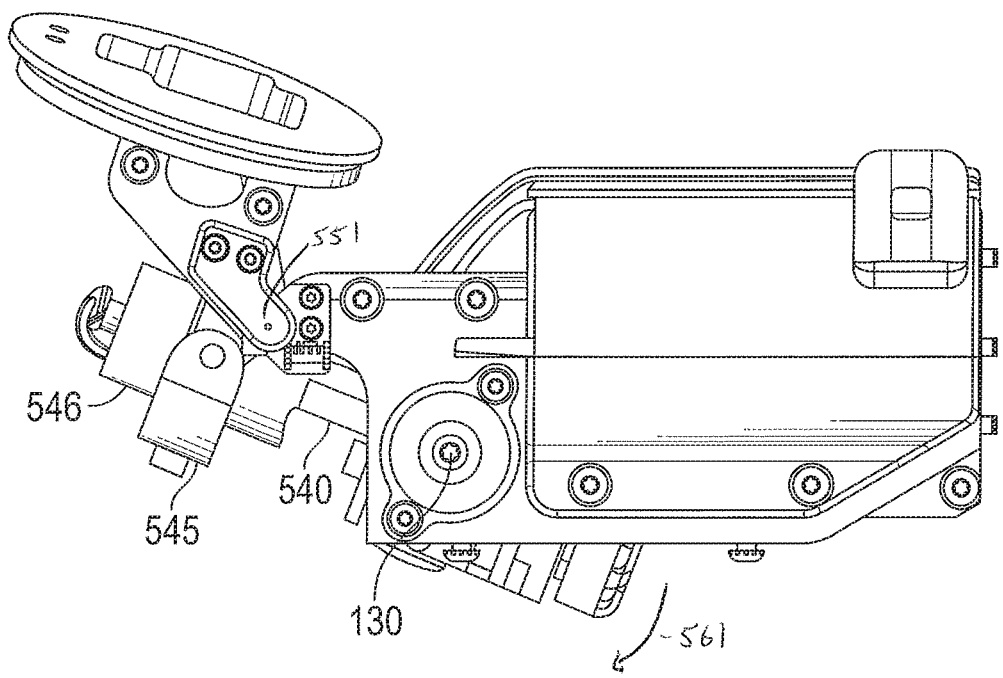
FIG. 18 shows the elbow of the prosthetic limb in a flexed position, according to an embodiment.

A roller screw nut 546 of the differential roller screw 540 pivots about hinge joint 130 and nut pivot 546, so that the differential roller screw 540 experiences axial loads but not bending moments. FIG. 17 shows elbow 50 extended and FIG. 18 shows elbow 50 flexed, with differential roller screw 540 pivoting about the hinge joint 130. The hinge joint 130 is encased in the bushing 120. In one embodiment, the bushing 120 is made of a nonlinear compliant material, such as rubber, rather than of a rigid material. When made of a nonlinear compliant material, the bushing 120's stiffness provides the elbow 50 with joint compliance similar to that of able-bodied persons when their elbows swing freely during walking. As a result, a user who walks while wearing limb 10 using a non-compliant bushing 120 experiences a more natural swinging movement. Additionally, the nonlinear nature of the compliance prevents the joint of the elbow 50 from deforming too far, such as when a user raises the limb 10 over her head or uses the limb 10 to push herself out of her seat.

Figure 19:
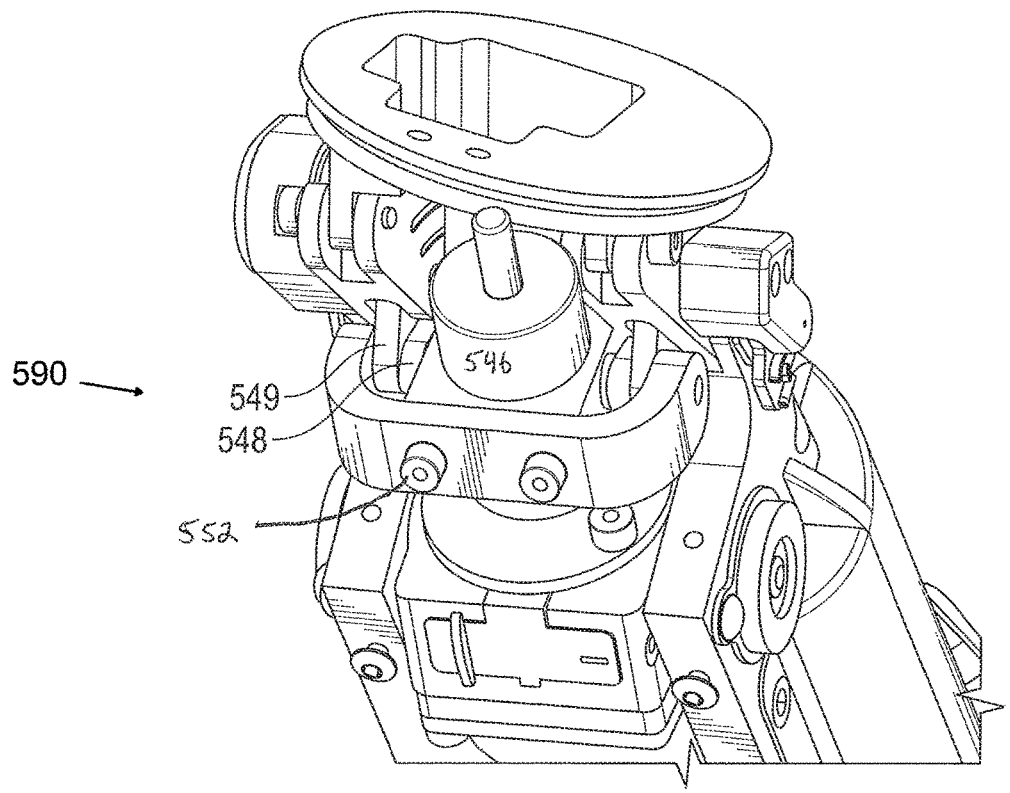
FIG. 19 shows a perspective view of the elbow of the prosthetic limb, according to one embodiment.
Figure 20:
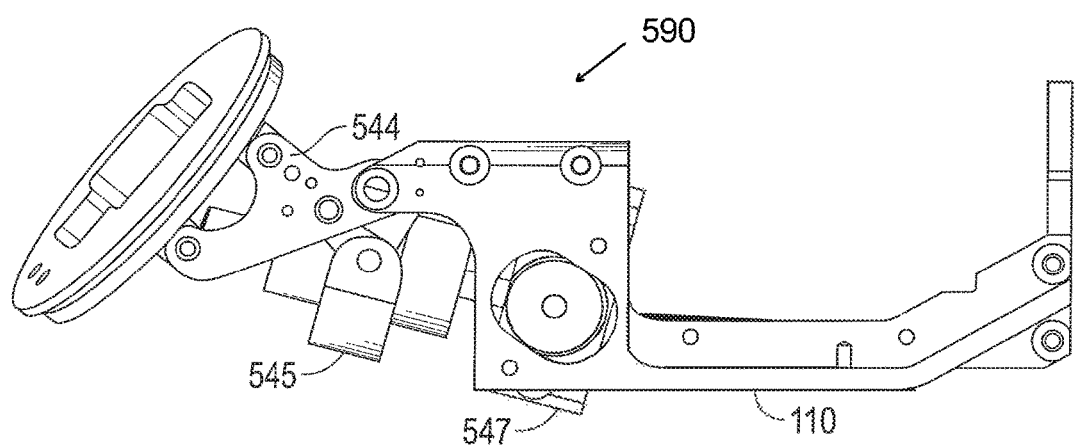
FIG. 20 shows a side view of the elbow of the prosthetic limb, according to one embodiment.

In an embodiment, the elbow 50 further comprises the elbow linkage 590 shown at FIGS. 19 and 20. In one embodiment, the elbow linkage 590 comprises the frame 110, the differential roller screw 540, a humeral frame 544, the roller screw nut 546, the thrust housing 547, a first nut link 548 and a second nut link 549. However, it should be understood that different link configurations could be used to assemble the elbow linkage 590. The elbow linkage 590 converts the linear motion of the differential roller screw 540 to rotary motion about the axis of rotation 560 of the elbow 50, via force applied thorough the roller screw bracket 545 and the roller screw nut 546. A user will typically use the limb 10 while in an upright position. As a result, the torque generated by gravitational forces is minimal when the elbow 50 is fully extended, as shown in FIG. 17, and is maximal when the elbow 50 is flexed 90 degrees. For this reason, the elbow linkage 590 has a kinematically defined non-constant gear ratio. The lengths of the four bars in the elbow linkage 590 may be optimized to minimize the linkage forces and the torque required to lift a constant weight from 0 to 135 degree range of motion of the elbow 50. The axis of the elbow linkage 590 is placed non-prismatically relative to socket connector 95, such that elbow 50 has a natural carrying angle that mimics the carrying angle in humans. FIG. 19 shows the socket connector 95 at such an angle. As shown in FIG. 19, this carrying angle creates medial humeral rotation when the elbow 50 is flexed, allowing the hand 30 to reach the midline of the body without the need for a separate humeral-rotator. Two shear pins (not shown) connecting the elbow linkage 590 break when the elbow 50 is subjected to excessive torque, to prevent potential damage to the differential roller screw 540. Excessive torque might result if a user falls on the limb 10 or from an external force applied to the limb 10. The placing of shear pins allows for the arm to fail gracefully when needed. The shear pins may easily be replaced by a clinician or service technician, allowing for relatively inexpensive repair.

FIG. 17 shows elbow 50 in a position of relative extension and FIG. 18 shows the elbow 50 in a position of relative flexion. As shown in FIGS. 15-20, in one embodiment, the elbow may comprise a first limb portion, which may comprise the humeral frame 544, and a second limb portion, which may comprise the frame 110, coupled together at the elbow joint 551. A first end of the screw 540 is coupled to the first limb portion, for instance by threading the first end of the screw 540 through the roller screw nut 546, which is attached to the roller screw bracket 545 by the screws 552. The transmission housing 550 is coupled to the humeral frame 544 at a transmission joint, which in one embodiment is the hinge joint 130. When the screw 540 extends linearly in a direction away from the transmission housing 550, the screw 540 applies a force on the roller screw bracket 545 via the roller screw nut 546, which causes the humeral frame 544 to rotate about the elbow joint 551 towards the humeral frame 544. The rotation of the first limb portion towards the second limb portion is also known as the flexion of the elbow. When the screw 540 retracts linearly in a direction towards the transmission housing 550, the screw 540 applies a force on the roller screw bracket 545 that causes the humeral frame 544 to rotate about the elbow joint 551 away from the frame 110. The rotation of the first limb portion away from the second limb portion is also known as the extension of the elbow. In one embodiment, as the screw 540 extends linearly in a direction away from the transmission housing 550, the transmission housing 550 rotates about the hinge joint 130 in a first direction. As shown in FIG. 18 in comparison to FIG. 17, the transmission housing 550 rotates about the hinge joint 130 in a clockwise direction indicated by arrow 561. When the screw 540 retracts linearly in a direction towards the transmission housing 550, the transmission housing 550 rotates about the hinge joint 130 in a second direction opposite to the first direction. As shown in FIG. 17 in comparison to FIG. 18, the transmission housing 550 rotates about the hinge joint in a counter-clockwise direction indicated by arrow 562.

In some of the embodiments described herein, the limb 10 conforms to the body size of a 25th percentile adult female (17.8 cm/7" hand circumference) and has a sufficiently small mass in order to be most suitable for smaller users, such as women or children. It should be understood that the design of the limb 10 and its associated components can be scaled to accommodate other sized users. The components of the limb 10 described herein may be used with other prostheses components. For instance, the hand 30, the wrist rotator 90, and the wrist flexor 70 may be coupled to a prosthetic forearm of another manufacturer.

Each papers and articles noted herein are hereby incorporated by reference and available for inspection in the records of the United States Patent and Trademark Office for this patent.

In view of the many possible embodiments to which the principles of the present discussion may be applied, it should be recognized that the embodiments described herein with respect to the drawing figures are meant to be illustrative only and should not be taken as limiting the scope of the claims. Therefore, the techniques as described herein contemplate all such embodiments as may come within the scope of the following claims and equivalents thereof.

What is claimed is:

1. A method of rotating a prosthetic elbow joint of a prosthetic upper limb comprising a proximal portion and a distal portion, the method comprising:
    aligning a screw, a motor and a transmission housing of the prosthetic upper limb along a first axis, wherein the proximal portion of the prosthetic upper limb is rotationally attached to the distal portion of the prosthetic upper limb about a third axis at the elbow joint, the third axis perpendicular to and offset ventrally from the first axis, and wherein a frame located in the distal portion of the prosthetic upper limb is rotationally attached to the transmission housing about a second axis that is perpendicular to the first axis and is located distal to the third axis;
    rotating the screw in a first direction about the first axis, the screw supported by the transmission housing of the prosthetic upper limb;
    translating a nut linearly relative to the screw and away from the transmission housing along the first axis in response to rotation of the screw in the first direction;
    rotating the screw and transmission housing relative to the frame about the second axis in response to the translation of the nut; and
    rotating the distal portion of the prosthetic upper limb relative to the proximal portion of the prosthetic upper limb in a first rotational direction about the third axis in response to the translation of the nut.

2. The method of claim 1, wherein rotating the distal portion of the prosthetic upper limb relative to the proximal portion of the prosthetic upper limb in the first rotational direction comprises rotating the distal portion of the prosthetic upper limb toward the proximal portion.

3. The method of claim 1, further comprising rotating the screw in a second direction opposite the first direction about the first axis, translating the nut linearly along the first axis in response to rotation of the screw in the second direction, and rotating the distal portion of the prosthetic upper limb relative to the proximal portion of the prosthetic upper limb in a second rotational direction about the third axis in response to translation of the nut, wherein the second rotational direction is opposite the first rotational direction.

4. The method of claim 3, wherein rotating the distal portion of the prosthetic upper limb relative to the proximal portion of the prosthetic upper limb in the second rotational direction comprises rotating the distal portion of the prosthetic upper limb away from the proximal portion.

5. The method of claim 3, wherein translating the nut linearly along the first axis in response to rotation of the screw in the second direction comprises moving the nut linearly towards the transmission housing that is rotatably coupled to the prosthetic upper limb.

6. The method of claim 1, further comprising actuating a transmission in response to rotation of the screw in the first direction about the first axis.

7. The method of claim 1, further comprising indicating rotational movement of the prosthetic elbow joint using a position sensor.

8. A method of rotating a prosthetic elbow joint of a prosthetic upper limb comprising a proximal portion and a distal portion, the method comprising:
   translating a nut linearly away from a transmission housing along a first axis, wherein the transmission housing is rotatably coupled to the distal portion of the prosthetic upper limb about a second axis that is perpendicular to the first axis;
   rotating the transmission housing relative to the prosthetic upper limb about the second axis in response to translation of the nut; and
   rotating the distal portion of the prosthetic upper limb relative to the proximal portion of the prosthetic upper limb in a first direction about a third axis in response to the translation of the nut, wherein the third axis is parallel to the second axis and offset ventrally from the first axis, and wherein the second axis is positioned between a distal end of the transmission housing and the nut.

9. The method of claim 8, wherein the transmission housing is rotatably coupled to the prosthetic upper limb via a frame.

10. The method of claim 8, wherein rotating the transmission housing relative to the prosthetic upper limb comprises rotating the housing relative to the distal portion of the prosthetic upper limb.

11. The method of claim 8, further comprising translating the nut linearly towards the transmission housing along the first axis and rotating the distal portion of the prosthetic upper limb relative to the proximal portion of the prosthetic upper limb in a second direction about the third axis in response to translation of the nut, wherein the second direction is opposite the first direction.

12. The method of claim 8, wherein rotating the distal portion of the prosthetic upper limb relative to the proximal portion of the prosthetic upper limb in the first direction comprises rotating the distal portion of the prosthetic upper limb toward the proximal portion of the prosthetic upper limb.

13. The method of claim 11, wherein rotating the distal portion of the prosthetic upper limb relative to the proximal portion of the prosthetic upper limb in the second direction comprises rotating the distal portion of the prosthetic upper limb away from the proximal portion of the prosthetic upper limb.

14. A method of rotating a prosthetic elbow joint, the method comprising:
   rotating a screw in a first direction about a first axis, the screw supported by a housing of a prosthetic upper limb;
   translating a nut linearly relative to the screw along the first axis in response to rotation of the screw in the first direction;
   rotating the screw and the nut relative to the prosthetic upper limb about a second axis in response to translation of the nut, wherein the second axis is perpendicular to the first axis; and
   rotating a distal portion of the prosthetic upper limb relative to a proximal portion of the prosthetic upper limb in a first rotational direction about a third axis in response to the translation of the nut, wherein the third axis is parallel to the second axis and offset ventrally from the first axis, and wherein the second axis is positioned between a distal end of the distal portion of the upper prosthetic limb and the nut.

15. The method of claim 14, further comprising rotating the screw in a second direction opposite the first direction about the first axis, translating the nut linearly along the first axis in response to rotation of the screw in the second direction, and rotating the distal portion of the prosthetic upper limb relative to the proximal portion of the prosthetic upper limb in a second rotational direction about the third axis in response to translation of the nut, wherein the second rotational direction is opposite the first rotational direction.

16. The method of claim 14, further comprising axially aligning the screw and the nut with a motor and a transmission housing.

* * * * *